US011375995B1

(12) United States Patent  
Tran et al.

(10) Patent No.: US 11,375,995 B1  
(45) Date of Patent: Jul. 5, 2022

(54) LOCKING SUTURE CONSTRUCT FOR TENSIONED SUTURE TO SUTURE STITCHES IN ANCHOR ARRAYS FOR ATTACHING SOFT TISSUE TO BONE

(71) Applicant: Integrity Orthopaedics, Inc., Orono, MN (US)

(72) Inventors: Nathaniel Van Tran, Lakeville, MN (US); Zak Zenz-Olson, Ham Lake, MN (US); Thomas A. Westling, Orono, MN (US); Howard W. Harris, Southlake, TX (US)

(73) Assignee: Integrity Orthopaedics, Inc., Orono, MN (US)

( * ) Notice: Subject to any disclaimer, the term of this patent is extended or adjusted under 35 U.S.C. 154(b) by 0 days.

(21) Appl. No.: 17/551,860

(22) Filed: Dec. 15, 2021

Related U.S. Application Data

(60) Provisional application No. 63/281,411, filed on Nov. 19, 2021, provisional application No. 63/172,568, filed on Apr. 8, 2021.

(51) Int. Cl.  
*A61B 17/04* (2006.01)  
*A61B 17/06* (2006.01)

(52) U.S. Cl.  
CPC .... *A61B 17/0469* (2013.01); *A61B 17/06166* (2013.01); *A61B 2017/0404* (2013.01); *A61B 2017/0409* (2013.01); *A61B 2017/0414* (2013.01); *A61B 2017/0446* (2013.01); *A61B 2017/0474* (2013.01); *A61B 2017/0496* (2013.01)

(58) Field of Classification Search  
None  
See application file for complete search history.

(56) References Cited

U.S. PATENT DOCUMENTS

| 4,899,743 A | 2/1990 | Nicholson et al. |
| 4,968,315 A | 11/1990 | Gatturna |
| 5,041,129 A | 8/1991 | Hayhurst et al. |
| 5,192,303 A | 3/1993 | Gatturna et al. |
| 5,203,787 A | 4/1993 | Noblitt et al. |
| 5,207,679 A | 5/1993 | Li |
| 5,269,809 A | 12/1993 | Hayhurst et al. |
| 5,403,348 A | 4/1995 | Bonutti |

(Continued)

*Primary Examiner* — Shaun L David  
(74) *Attorney, Agent, or Firm* — Seager, Tufte & Wickhem, LLP

(57) ABSTRACT

An assembly and method are provided for incorporation into suture anchor designs to facilitate the locking of a slidable working suture after it has been tensioned. The assembly can be utilized on multiple anchors in a pre-strung chain on a single working suture to create continuous, individually tensioned suture bridges between anchors in series, without knot tying. Further, the bridges are independently locked with selected tension for the particular application. An anchor body having at least one suture receiving passage therethrough is threaded with a working suture wherein the working suture flosses through the passage when tension is applied to the working suture. A locking cord extends through a second passage through the anchor body, the locking cord having a collapsible loop extending out the second passage and encircling a portion of the working suture, wherein collapsing the loop locks the working suture after tensioning.

20 Claims, 33 Drawing Sheets

(56) References Cited

U.S. PATENT DOCUMENTS

| | | | |
|---|---|---|---|
| 5,405,359 A * | 4/1995 | Pierce | A61B 17/0401 606/232 |
| 5,468,197 A | 11/1995 | Loeffler | |
| 5,584,835 A | 12/1996 | Greenfield | |
| 5,626,614 A | 5/1997 | Hart | |
| 5,669,935 A | 9/1997 | Rosenman et al. | |
| 5,683,418 A | 11/1997 | Luscombe et al. | |
| 5,725,557 A | 3/1998 | Gatturna et al. | |
| 5,728,100 A | 3/1998 | Skiba | |
| 5,741,300 A | 4/1998 | Li | |
| 5,810,848 A | 9/1998 | Hayhurst | |
| 5,891,168 A * | 4/1999 | Thal | A61F 2/0811 606/232 |
| 5,921,986 A | 7/1999 | Bonutti | |
| 5,948,002 A | 9/1999 | Bonutti | |
| 5,961,538 A | 10/1999 | Pedlick et al. | |
| 6,056,773 A | 5/2000 | Bonutti | |
| 6,066,160 A | 5/2000 | Colvin et al. | |
| 6,117,161 A | 9/2000 | Li et al. | |
| 6,270,518 B1 | 8/2001 | Pedlick et al. | |
| 6,293,961 B2 | 9/2001 | Schwartz et al. | |
| 6,451,030 B2 | 9/2002 | Li et al. | |
| 6,500,195 B2 | 12/2002 | Bonutti | |
| 6,520,980 B1 | 2/2003 | Foerster | |
| 6,527,795 B1 | 3/2003 | Lizardi | |
| 6,547,800 B2 | 4/2003 | Foerster et al. | |
| 6,592,609 B1 | 7/2003 | Bonutti | |
| 6,645,227 B2 | 11/2003 | Fallin et al. | |
| 6,660,023 B2 | 12/2003 | McDevitt et al. | |
| 6,726,707 B2 | 4/2004 | Pedlick et al. | |
| 6,773,436 B2 | 8/2004 | Donnelly et al. | |
| 6,843,799 B2 | 1/2005 | Bartlett | |
| 6,972,027 B2 | 12/2005 | Fallin et al. | |
| 6,986,781 B2 | 1/2006 | Smith | |
| 7,041,120 B2 | 5/2006 | Li et al. | |
| 7,081,126 B2 | 7/2006 | McDevitt et al. | |
| 7,232,455 B2 | 6/2007 | Pedlick et al. | |
| 7,320,701 B2 | 1/2008 | Haut et al. | |
| 7,556,640 B2 | 7/2009 | Foerster | |
| 7,566,339 B2 * | 7/2009 | Fallin | A61B 17/0487 606/103 |
| 7,641,672 B2 | 1/2010 | Fallin et al. | |
| 7,645,293 B2 | 1/2010 | Martinek et al. | |
| 7,674,275 B2 | 3/2010 | Martin et al. | |
| 7,682,374 B2 | 3/2010 | Foerster et al. | |
| 7,722,644 B2 * | 5/2010 | Fallin | A61B 17/0487 606/103 |
| 7,806,909 B2 * | 10/2010 | Fallin | A61B 17/0487 606/232 |
| 7,875,064 B2 | 1/2011 | Donnelly et al. | |
| 7,909,851 B2 | 3/2011 | Stone et al. | |
| 7,963,972 B2 | 6/2011 | Foerster et al. | |
| 8,052,719 B2 | 11/2011 | Paulos | |
| 8,118,835 B2 | 2/2012 | Weisel et al. | |
| 8,298,262 B2 | 10/2012 | Stone et al. | |
| 8,348,975 B2 | 1/2013 | Dreyfuss | |
| 8,366,744 B2 | 2/2013 | Bojarski et al. | |
| 8,419,794 B2 | 4/2013 | ElAttrache et al. | |
| 8,425,536 B2 | 4/2013 | Foerster et al. | |
| 8,449,584 B2 | 5/2013 | Donnelly et al. | |
| 8,454,655 B2 | 6/2013 | Yeung et al. | |
| 8,512,375 B2 | 8/2013 | Torrie et al. | |
| 8,771,314 B2 | 7/2014 | Crombie et al. | |
| 8,777,992 B2 | 7/2014 | Yeung et al. | |
| 8,828,052 B2 | 9/2014 | Caborn et al. | |
| 8,845,699 B2 | 9/2014 | Bonutti | |
| 8,932,331 B2 | 1/2015 | Kaiser et al. | |
| 8,951,287 B1 | 2/2015 | Green et al. | |
| 8,986,346 B2 | 3/2015 | Dreyfuss | |
| 9,072,509 B2 | 7/2015 | Stoll, Jr. et al. | |
| 9,173,651 B2 | 11/2015 | Stone et al. | |
| 9,192,369 B2 * | 11/2015 | Bittenson | A61B 17/0401 |
| 9,216,036 B2 | 12/2015 | Johnstone | |
| 9,220,493 B2 | 12/2015 | Hart et al. | |
| 9,265,495 B2 | 2/2016 | Petersen et al. | |
| 9,271,714 B2 | 3/2016 | Martin | |
| 9,301,756 B2 | 4/2016 | Wardle | |
| 9,307,979 B1 | 4/2016 | Bennett et al. | |
| 9,314,238 B2 | 4/2016 | Martin | |
| 9,345,467 B2 | 5/2016 | Lunn et al. | |
| 9,451,945 B2 | 9/2016 | Hawkins | |
| 9,463,008 B2 | 10/2016 | Thal | |
| 9,504,462 B2 | 11/2016 | Dooney, Jr. et al. | |
| 9,526,489 B2 | 12/2016 | Burkhart | |
| 9,532,777 B2 | 1/2017 | Kaiser et al. | |
| 9,539,000 B2 | 1/2017 | Hendricksen et al. | |
| 9,545,251 B2 | 1/2017 | Bojarski et al. | |
| 9,597,070 B2 | 3/2017 | Bittenson | |
| 9,655,611 B2 | 5/2017 | Green et al. | |
| 9,693,765 B2 | 7/2017 | Sullivan et al. | |
| 9,713,463 B2 | 7/2017 | Oren et al. | |
| 9,763,719 B2 | 9/2017 | Snyder et al. | |
| 9,814,565 B2 | 11/2017 | Foerster et al. | |
| 9,872,678 B2 | 1/2018 | Spenciner et al. | |
| 9,931,150 B2 | 4/2018 | Philippon et al. | |
| 10,130,354 B2 | 11/2018 | Dooney, Jr. | |
| 10,172,607 B2 | 1/2019 | Burkhart | |
| 10,178,989 B2 | 1/2019 | Bennett et al. | |
| 10,285,684 B2 | 5/2019 | Spenciner et al. | |
| 10,368,856 B2 | 8/2019 | Stone et al. | |
| 10,376,260 B2 | 8/2019 | Bojarski et al. | |
| 10,398,428 B2 | 9/2019 | Denham et al. | |
| 10,478,172 B1 | 11/2019 | Williams et al. | |
| 10,543,075 B2 | 1/2020 | Gregoire et al. | |
| 10,575,842 B2 | 3/2020 | Lund | |
| 10,588,614 B2 | 3/2020 | Gittings et al. | |
| 10,603,029 B2 | 3/2020 | Kaiser et al. | |
| 10,667,803 B2 | 6/2020 | Lizardi | |
| 10,675,015 B2 | 6/2020 | Guo et al. | |
| 10,729,421 B2 | 8/2020 | Stone et al. | |
| 10,772,622 B2 | 9/2020 | Santangelo et al. | |
| 10,786,235 B2 | 9/2020 | Sorensen et al. | |
| 10,863,979 B2 | 12/2020 | Sorensen et al. | |
| 10,952,719 B2 | 3/2021 | Lombardo et al. | |
| 10,966,704 B2 | 4/2021 | Lozier et al. | |
| 10,987,099 B2 | 4/2021 | Stone et al. | |
| 2004/0002734 A1 * | 1/2004 | Fallin | A61B 17/0401 606/232 |
| 2005/0288711 A1 * | 12/2005 | Fallin | A61B 17/0401 606/232 |
| 2006/0178702 A1 | 8/2006 | Pierce et al. | |
| 2008/0065114 A1 * | 3/2008 | Stone | A61B 17/0401 606/279 |
| 2009/0312782 A1 | 12/2009 | Park | |
| 2011/0022061 A1 * | 1/2011 | Orphanos | A61B 17/0469 606/232 |
| 2011/0160856 A1 * | 6/2011 | Sinnott | A61F 2/0811 623/13.14 |
| 2012/0046747 A1 * | 2/2012 | Justin | A61B 17/0401 606/232 |
| 2012/0078299 A1 * | 3/2012 | Ramos Clamote | A61B 17/0218 606/232 |
| 2013/0096611 A1 * | 4/2013 | Sullivan | A61B 17/0485 606/232 |
| 2013/0190815 A1 | 7/2013 | Mansmann | |
| 2013/0197580 A1 * | 8/2013 | Perriello | A61B 17/0401 606/232 |
| 2013/0345750 A1 * | 12/2013 | Sullivan | A61F 2/0811 606/232 |
| 2014/0052179 A1 * | 2/2014 | Dreyfuss | A61F 2/08 606/232 |
| 2014/0257346 A1 * | 9/2014 | Sengun | A61B 17/0401 606/148 |
| 2015/0039026 A1 * | 2/2015 | Pasquali | A61B 17/0401 606/228 |
| 2015/0157449 A1 * | 6/2015 | Gustafson | A61B 17/06166 606/232 |
| 2015/0196385 A1 * | 7/2015 | Kam | A61F 2/0811 623/13.14 |
| 2015/0250470 A1 | 9/2015 | Vargas | |

(56) References Cited

U.S. PATENT DOCUMENTS

| | | | |
|---|---|---|---|
| 2016/0113642 A1* | 4/2016 | Pilgeram | A61B 17/0485 |
| | | | 606/232 |
| 2016/0157851 A1* | 6/2016 | Spenciner | A61F 2/0811 |
| | | | 606/232 |
| 2019/0099258 A1* | 4/2019 | Armington | A61B 17/06166 |
| 2020/0253715 A1 | 8/2020 | Trenhaile | |
| 2020/0281712 A1* | 9/2020 | Kam | A61B 17/0401 |
| 2020/0315774 A1* | 10/2020 | Snedeker | A61B 17/0401 |
| 2020/0315775 A1 | 10/2020 | Pilgeram et al. | |

\* cited by examiner

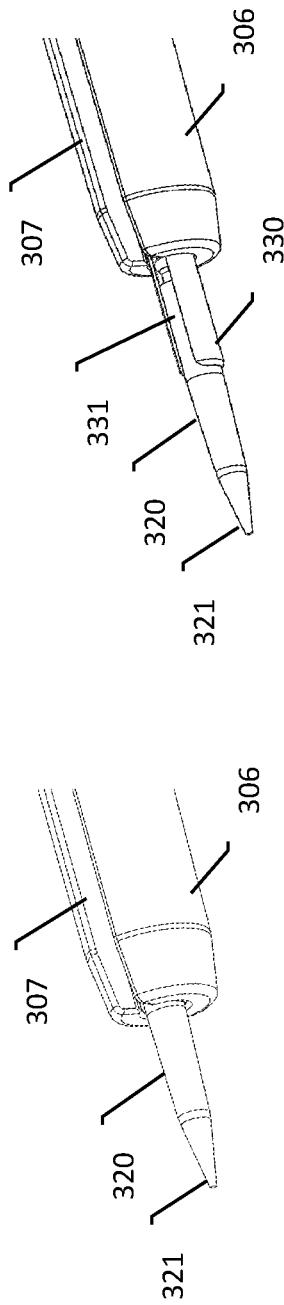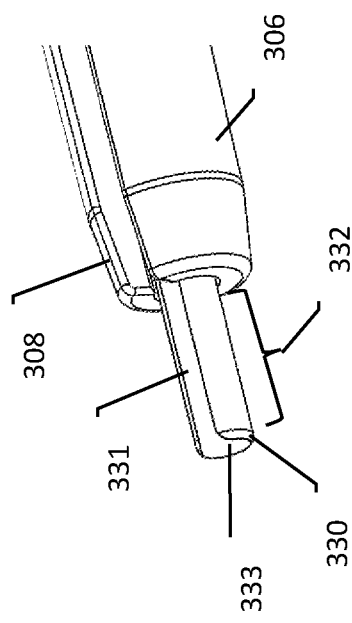
Figure 3D
Figure 3E
Figure 3F

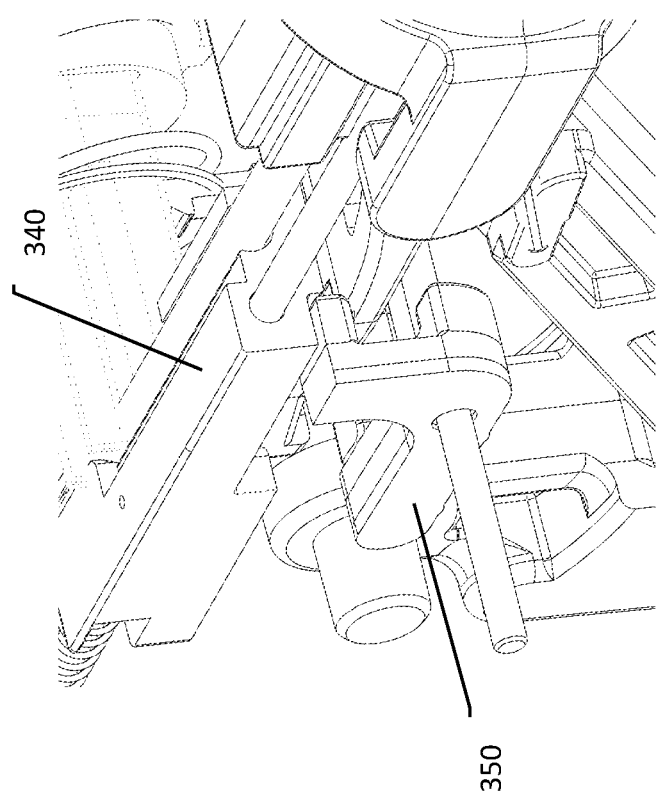

LOCKING SUTURE CONSTRUCT FOR TENSIONED SUTURE TO SUTURE STITCHES IN ANCHOR ARRAYS FOR ATTACHING SOFT TISSUE TO BONE

CROSS REFERENCE TO RELATED APPLICATIONS

The present application claims the benefit of and priority to U.S. Prov. Pat. App. No. 63/172,568, filed Apr. 8, 2021, and titled LOCKING SUTURE CONSTRUCT FOR TENSIONED SUTURE TO SUTURE BRIDGES IN ANCHOR ARRAYS FOR ATTACHING SOFT TISSUE TO BONE, and U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosures of which are incorporated herein by reference.

BACKGROUND

Throughout the human body there are many attachments of soft tissue, such as tendons and ligaments, to bone as integral elements of motion in functioning joints such as the shoulder. The shoulder joint includes the humeral head of the upper arm bone in contact with the indentation of the glenoid working in conjunction with the rotator cuff, which is a combination of muscles and tendons forming a capsule that both stabilizes the joint and causes desired motion. Injury to the connection between tendons of the rotator cuff muscles to the humeral head, usually a tear in a tendon, is common. These tears do not self-heal. It is estimated that in the U.S. over 4 million people annually are referred to a surgeon due to shoulder pain and over 500,000 of these referrals result in shoulder surgery to repair the rotator cuff.

Significant effort has been expended over the past 30 years to develop bone and tissue anchor devices and methods to respond to the need for effective rotator cuff repair. Early methods and devices utilized an open surgical technique that required a large incision of 4 to 6 cm and cutting the deltoid muscle, then re-attaching after the rotator cuff repair. This method is still used today for massive tears by some surgeons due to high success rate, however, the procedure is associated with deltoid dysfunction, significant pain during recovery and extensive rehabilitation time. Due to the invasiveness of the open surgery and resulting rehabilitation time, a "mini-open" procedure and associated devices were developed in the early 1990's, wherein the surgeon uses partial arthroscopic techniques followed by an incision and split of the deltoid muscle fibers to access the rotator cuff tendon for repair. By the late 1990's, devices and instruments were further developed to complete the repair of rotator cuff tendon attachment to bone using all-arthroscopic techniques, with further resultant reduction in trauma and recovery time.

Arthroscopic repair of the rotator cuff tendon attachments to the humeral head are the most common technique used today. However, it is recognized that these all-arthroscopic techniques are quite difficult to perform and achieve varying results. The skill of the surgeon with the technology available is a known factor related to the procedure's success. Even with the last 20 years of all-arthroscopic technologic advancement and experience, deficiencies persist as evidenced by studies indicating an overall average rotator cuff repair failure rate of 20% to 40%, with a highly variable range of 4% to 90% in individual studies. The study results indicate failure rates are much higher for large or massive tendon tears and there are vast variations in failure rates between surgeons, as well as with respect to various patient factors, equipment used, and type of repair completed.

There is significant controversy among professionals as to the reasons for the high incidence of arthroscopic rotator cuff repair failure (i.e. "re-tear of the rotator cuff"). However, studies clearly show there is a need to reduce the failure rate of arthroscopic rotator cuff repair to avoid its effects of patients' lack of mobility, functional deficits, increased pain and/or requiring subsequent and more invasive surgery with the attendant pain and rehabilitation. In particular, there is great concern for patients who have some degree of native tendon or repair tendon failure yet choose to "live with it" rather than going through a first or additional surgery and rehabilitation, thus affecting quality of life and promoting continued joint degradation from lack of use.

The basic device or devices used for repair of a tendon torn from a bone is one or more suture anchors in which a mechanical structure provides an anchor to the bone and a suture or sutures extend therefrom for attachment to the soft tissue or tendon. Many types of anchor technologies have been proposed and used in procedures. A review of the prior art patent literature indicates over a thousand designs for suture anchors, bone anchors, tendon repair systems, delivery devices and methods espousing improved features over the past 25 years, yet repair failure rate is still unacceptable indicating the need for further improvement in the area of arthroscopic reattachment of tendons to bone and in particular in rotator cuff repair.

Overview

The present inventors have recognized, among other things, that a problem to be solved is the need for new and/or alternative devices and methods for arthroscopically affixing a tendon or other soft tissue to bone, such as in rotator cuff repair, with low failure rate, preferably under 10% on average, with little variation between surgeons, patient characteristics, and the system/method used for repair. The disclosed devices, systems, and methods, along with a statement of the problem being solved by each element are included in summary form followed by a description of specific claimed structure or methods in the present disclosure.

The present disclosure includes a total system for re-attaching a tendon that has at least in part torn away from a bone attachment or footprint. The system is useful in repair of a rotator cuff tendon that has torn away from a bone but can be used in other soft tissue and tendon repair procedures. The system is particularly useful in repair of the rotator cuff by reattaching a torn tendon, such as the most-commonly-torn supraspinatus tendon, to the humeral head of the arm. In larger tears, the infraspinatus tendon may also be torn and amenable to repair with this system. The repair is an anatomical repair, meaning that the system, devices and methods result in a repaired tendon and bone combination that closely approximates the prior natural, anatomic relationship between that tendon and bone to promote healing and provide pain-free full function to the healed repair. An anatomical repair using the presently described system may also seal the tendon in position, taking advantage of local synovial fluid to aid healing and improve post-surgery function. The system may also be used to reinforce partial tears and to secure areas beyond the region of a full-thickness tear as needed. Further, the system, as implanted can dramatically reduce recovery and rehabilitation time due to the robust nature of the repair immediately following surgery, requiring less time using a sling to limit mobility and allowing early physical therapy to maintain pre-surgery mobility and strength during healing. It is believed time in a sling and complete recovery time can be reduced at least 50%, while reducing the average failure rate to less than 10% with the current disclosed system.

As stated, in preferred examples, the exemplary rotator cuff repair is an anatomical repair in that the repaired tendon nearly duplicates or closely approximates the natural tendon and bone relationship in the fully functional joint. For example, the tendon/tendons is/are substantially and completely re-attached to the original footprint on the bone from which it was torn. The original footprint area provides the greatest likelihood of healing re-attachment of the tendon to the bone while restoring anatomy. By substantially re-attached to the original footprint it is meant that a substantial portion of the remaining torn tendon surface that was originally attached to the footprint is re-attached thereto. The current system makes possible close approximation of the original tendon attachment by allowing transtendinous or through the tendon implantation of each anchor. Thus, the tendon is held in the desired location when the anchor is installed, unlike current systems that insert anchors into exposed bone through a tear and then use suture passers (which pass the suture when the tendon is not in position) to approximate where the surgeon believes the tendon will pull down to the footprint. Further, the anatomical repair reduces micromotion at the bone to tendon interface so that healing is promoted, even during movement of the joint. Finally, access to blood for healing is improved due to utilizing substantially more small holes in the proximal humerus that are not occluded by the implant sutures to accommodate a large number of anchors in a close or high-density array.

In fresh cadaveric studies using the presently disclosed system, the repaired tendon and bone combination provides a tensile strength upon re-attachment of greater than 400 Newtons (N) and initial cyclic creep or gap formation of less than 2 millimeters (mm) when cycled to a peak load on the repaired tendon per cycle of 180 N. Initial cyclic creep measures the rigidity or robustness of the attachment of the tendon to the bone as it measures how much the tendon slides or moves relative to the bone attachment. Low initial cyclic creep allows the potential for faster healing and less need for sling immobilization. Creep of less than 2 mm, or even less than 1 mm, is therefore a preferred outcome in some examples. In other words, if the tendon stays fixed in position relative to the bone it is compressed against (i.e. reduced micromotion), the healing process will occur more quickly and predictably than a situation that includes sliding of the tendon back and forth relative to the bone.

In selected embodiments, the anatomic repair requires a high-density array of knotless small anchors (requiring a bone hole size for insertion of less than 3 mm) with close spacing between anchors (less than 7 mm edge to edge, or less than 10 mm hole center to hole center) to create anchor to subsequent anchor or serial anchor suture stitches that apply many points of constant independent force on the tendon against the bone. By independent it is meant that failure of one suture stitch to apply adequate force, as would happen if the suture stitch broke, does not affect other suture stitches. Naturally, the number of anchors utilized in a repair will depend upon the size of the tear.

It is recognized in the art that rotator cuff tears are classified into four categories based on tear size and whether a single row or double row repair is completed. Small tears are less than 1 centimeter (cm) in length; medium tears are 1 cm to 3 cm in length; large tears are 3 cm to 5 cm in length and massive tears are greater than 5 cm in length. With current devices, surgeons are limited to available large anchors and by the size of the tear as the medial anchors must fit in the tear area that exposes bone. For example, surgeons may use about 1 medial anchor on small tears, 1 or 2 medial anchors on medium tears and 2 or 3 medial anchors on large tears and massive tears. With the high anchor density anatomical repair of the present application, the surgeon is not limited by tear size as the anchors are implanted through the tendon and can use greater than 3 medial anchors on small tears, greater than 5 medial anchors on medium tears, and greater than 6 medial anchors on large tears and massive tears. This can include positioning implants outside the area of a full thickness tear to reinforce areas of partial thickness tears or weaker untorn tendon. Further, the present suture anchors are designed for knotless tensioning and locking to expedite implantation, maximize reproducibility amongst surgeons, and not interfere with shoulder mobility from protruding knots while eliminating the tension variations that have been found in knotted suture anchors due to the difficulty of tying knots arthroscopically.

The suture anchors of the present disclosure are bar or toggle type anchors wherein the basic structure for bone attachment is a thin elongate and/or cylindrical body having a cross sectional diameter of less than about 3 mm and a length of about 6 mm to about 10 mm. Alternative sizes could be used in other applications in the body as desired. Although described as generally cylindrical, it is recognized that certain surfaces can be machined or molded flat or grooved to allow for suture strands to run alongside the implant when placed in a circular delivery tube. That is, rather than cylindrical, the present anchors may be polygonal, for example, hexagonal or octagonal, or other cross-sectional shape. The anchor is a through the tendon or transtendinous implant as described with respect to the delivery device and method below. Being transtendinous eliminates the requirement of placing the anchors only where the tendon is absent from the bone such as in the hole formed by the tear or outside the tendon footprint. Furthermore, and importantly, the need for suture passing through the tendon is eliminated.

Transtendinous implantation with anchors used today entails technical challenges, including working a 3 mm to 6 mm diameter anchor through a hole created in the tendon with an awl, damaging the tendon. Further, threaded and flanged type anchor retention features of known, larger anchors, would damage the tendon during passing.

With a toggle type anchor, the anchor is inserted through a hole in the bone just larger than the anchor axial outer diameter. Within the bone, the anchor is toggled (aka flipped or rotated) about 90 degrees, but at least 60 degrees so that force applied to sutures extending from the toggle body pull the length of the toggle body against the inner surface or underside of the cortical shell of the humeral head. The degree to which the toggle body rotates or moves toward the cortical shell is affected by the quality of the bone and by individual patient traits, such as age, sex, location of the hole in the bone and degree of bone degradation due to the tear. The toggle body of the current invention is designed to toggle and seat with adequate pullout strength over the range of bone qualities encountered.

The toggle body functions in conjunction with a single suture line, referred to herein as the working suture which passes through at least one passage formed through the toggle body. The number of passages can be varied in the design of the toggle body as can the way in which the working suture is threaded through the passages to provide desired tensioning and locking functions. In some embodiments the toggle body includes three holes passing through the toggle body generally perpendicular to the longitudinal axis. In this embodiment the working suture passes through the top and out the bottom of a proximal hole, then back up through the bottom of a distal hole and out the top. The working suture is flossable or slidable as positioned through the two holes by pulling with sufficient force on either working suture leg extending out the top of the toggle body. On the bottom surface of the toggle body, a length of working suture extends longitudinally past the middle hole. A suture lock, which includes a separate piece of suture or thread or other flexible cord extends through the center hole, with an adjustable or collapsible loop or slidable knot which allows the loop to be contracted, extending around the perimeter of a portion of the working suture as it passes the middle hole. The other end of the suture lock cord extends from the top of the center hole. When the top end or proximal end of the suture lock is pulled, the adjustable loop collapses tight against the working suture and can pull at least a portion of the working suture into the center hole to create a lock on the working suture so that it can no longer slide and will not slide under full load as implanted.

In some embodiments, the tightening of the suture lock pulls a small portion of the working suture into a slot or channel in the bottom of the middle hole in the anchor. The working suture is pinched in a tortuous path that provides a sound lock and prevents sliding of the working suture relative to the anchor once the suture is appropriately tensioned. The strength of the lock is enhanced by the overall tortuous path followed by the working suture when the anchor is pulled against the cortical shell as the working suture goes through several near 90-degree turns which provide increased friction against the toggle body as well as the friction applied by the suture lock.

Each individual anchor includes features that assure it will implant properly through the tendon in a hole punched through the cortical shell of the humeral head. The anchor is inserted lengthwise through this hole into the spongy or cancellous bone. It is pushed by the point of a bone punch that mates with a dimple formed in the proximal end of the implant. The mating surface dimple is shaped to help maintain contact between the anchor and the punch while also allowing the anchor to pivot, rotate, or toggle from an insertion configuration in which the central axis of the anchor is aligned with the central axis of the punch to an implant configuration in which the central axis of the anchor no longer aligns with the central axis of the punch. The rotation or toggling may have two parts: an initial change of axial direction as the anchor passes beyond the cortical shell into the cancellous bone during advancement as the punch is used to push the anchor, and a second change of axial direction under tension applied using the working suture as described below. The cancellous bone varies greatly in properties by location and patient ranging from very soft and porous to hard cellular structures depending upon many patient-specific factors. The included features of the present anchor assure proper toggled retention within the bone over the range of cortical shell and cancellous bone variations.

In selected embodiments, the implant preferably includes an acute angle on the distal surface with the upper side projecting further longitudinally than the lower side. Inserted this way, the longer portion engages the cancellous bone and begins rotation during anchor insertion. With both the distal and proximal portion of the working suture extending up through the bone hole, one can pull the distal working suture selectively, which further rotates the implant body. In some examples the rotation may be to an angle of about 90 degrees relative to the central axis of the bone hole, though this extent of rotation is not necessary to the inventive concept. It has been found that in hard cancellous bone, the pulling on the distal suture at times may not cause rotation because the proximal portion is held rigid by a hard layer of cancellous bone and therefore pulling causes the toggle body to back out of the hole and lie under the tendon. To prevent this, the implant includes a fin or fins on the proximal portion that upon delivery project proximally and radially with a cross dimension greater than that of the bone hole. The size of the fins prevents back out of the anchor but also the fins are located to project and to catch on the cancellous bone and assist in rotation. The fins alone may not accommodate the full pullout force in some examples, rather the toggle anchor must rotate as well so that the force pulling on the anchor is carried by the side wall of the toggle body as rotated.

The single working suture is pre-strung through a plurality of anchors to be used as a set to form an implanted array having a tensioned suture stitch extending from one anchor to the subsequent anchor in the pre-strung chain. As previously stated, each anchor is slidable or flossable with sufficient force applied to move along the working suture. Each anchor is equipped with a suture lock as described above, except the first anchor in the chain which can have a standard suture lock or a fixed non-slidable suture connection. A chain of anchors can carry in the range of about 8 to 12 anchors in some preferred embodiments.

The high-density array of anchors is formed by implantation of the anchors in a chain or row which can be a relatively straight line or curve depending upon the tear to be repaired at the discretion of the surgeon. A delivery device system designed for sequential transtendinous implantation of each anchor in the array is disclosed herein as well. The delivery system includes a delivery tool distal portion to be used at the surgical site for implantation of the array, and a proximal portion having a handle and features for managing the anchors and associated sutures and suture lock. The distal portion of the delivery tool includes an anchor delivery tube sized to allow passage of an anchor and associated working suture and suture lock therethrough. The delivery tool is used with a bone punch that is sized as well for passage through the anchor delivery tube. The proximal portion of the delivery tool is configured to allow a physician to introduce an anchor that is pre-strung onto the working suture into the anchor delivery tube. The proximal portion of the delivery tool may include a platform for receiving a magazine carrying a number of cartridges that house the pre-strung anchors individually. The magazine may include a cartridge ejector that allows one cartridge at a time to be removed from the magazine and placed in a slot on the delivery tool. A plunger is used to transfer individual anchors from the cartridge to a lumen at the proximal end of the anchor delivery tube.

In use, the physician places the distal end of the delivery tool at a desired location for introduction of an anchor. Such placement may be performed with the bone punch extending past the distal end of the delivery tool to allow a physician to probe the desired location using the bone punch. The physician then presses the delivery tool distal end against the tendon and applies a force, such as by pounding, against the proximal end of the bone punch to create a path through the tendon and then to create a bone hole. The distal end of the anchor delivery tube, referred to as a nub, may be advanced through the tendon and at least partly into the bone hole as the bone punch is pounded.

The bone punch is then retracted, while the nub is kept in place to maintain registration through the tendon and into the bone hole. With the bone punch retracted, a cartridge is removed from the magazine using the cartridge ejector and transferred to the slot on the proximal portion of the delivery tool, and the plunger is depressed to move an anchor from the cartridge into position for advancement into the anchor delivery lumen. The bone punch is again advanced, this time pressing against the proximal end of the anchor, eventually ejecting the anchor from the anchor delivery tube into the bone hole. As the bone punch pushes the anchor down the anchor delivery tube, the tip of the bone punch is engaged with the dimple. The anchor delivery tube may be sized, relative to the anchor, to compress the fins as the anchor passes through the anchor delivery tube to a reduced outer dimension.

When the anchor exits the anchor delivery tube, the fins expand to their full relaxed diameter, reducing the potential for the anchor to back out of the bone hole. In some examples, the relaxed diameter of the fins is larger than the size of the bone hole. The bone punch is advanced so that the tip of the bone punch extends beyond the nub, forcing the anchor into the bone. As the anchor advances into bone, the angled distal surface enters the bone first, and begins to turn or toggle the anchor. The dimple is configured to allow the anchor to turn without torqueing against the distal tip of the bone punch, allowing the anchor to toggle as it is advanced. The bone punch is then retracted into the anchor delivery tube, and the working suture is manipulated to continue toggling the anchor into a position which is preferably parallel to the bone surface, though less than complete toggling may still provide a usable anchor position particularly in harder bone. To prevent interference between the anchor and the anchor delivery tube and/or damage to the working suture during toggling of the anchor, the anchor delivery tube may be retracted so that the nub is within the delivery tool. In addition, retracting the anchor delivery tube and/or nub can reduce flossing tension, allowing flossing of the working suture until tensioned; once tensioned relative to a prior anchor, toggling is further aided.

On this first anchor only, the working suture may be locked into position using the locking suture prior to using the working suture to toggle the anchor, or even prior to starting implant of the first anchor, if desired, as no anchor to anchor stitch can be formed until a second anchor is implanted. In some examples, the first anchor may be affixed to the working suture, and the locking suture may be omitted for the first anchor. When the first anchor is set in sufficiently strong material inside the bone (which can be harder cancellous bone or may be resting against the under surface of the cortical shell) the delivery device can be set with the punch pin partially extended as it was at the beginning of the procedure and moved for implantation of the next anchor.

With the second and subsequent anchors, both a proximal and a distal suture portions of the working suture extend up through the delivery device. It is the distal portion of the working suture that is pulled to cause rotation of the anchor while also allowing the working suture to slide through both holes in that anchor and the slack extending to the distal hole of the previous anchor is therefore shortened. It is also recognized that the proximal portion of the working suture can be tensioned in some embodiments to aid in rotating and seating the anchor in proper position within the bone hole. During toggling of the anchor and subsequent tensioning of the suture, the distal end of an outer tube of the delivery tool may be pressed against the tendon to provide a counterforce against pullout. This is continued until the properly tensioned suture stitch is formed at which point the suture lock on the second or subsequent anchor is activated to maintain tension in the individual suture stitch. The locking suture proximal extension can be cut off after tightening or a selectively breakable suture can be used and such breakable portion is positioned proximate to and proximal of the slidable knot.

This is repeated for a desired number of anchors in the pre-strung chain which is implanted to form a high-density array as described above. As can be understood, the number of suture stitches formed is equal to the number of anchors in the chain implanted minus 1. Further, the string of stitches is serially continuous with each stitch tensioned and locked independently to form a required robust tendon attachment. The continuous string of stitches can form a row or chain of stitches of desired shape such as a linear row, a zig-zag shape, an arc, etc. By row or chain, it is meant that the suture stitches extend from one anchor to the next in the sequence of implanted anchors. It is understood that more than one continuous string of stitches can be formed by implanting multiple anchor arrays that together form an overall repair array, especially for large tears.

As previously stated, the distance between ends of a suture stitch (the distance between anchors) is preferably less than about 7 mm (less than about 10 mm from center of hole to center of hole) to provide consistent force on the tendon against the bone to reduce creep. One particularly robust array of implanted anchors includes a first array implanted in a medial portion of the original tendon footprint to form a row or line of stitches generally perpendicular to the length or direction of the tendon's forces. A second array can then be implanted laterally nearer the edge of the tear with at least one anchor through the tendon while at least one other anchor is implanted laterally of the tendon edge to reapproximate the tendon properly against the bone. The lateral row can be implanted in a zig zag pattern or other appropriate pattern based on the shape of the tear. Depending upon tear size and location, multiple patterns can be utilized.

As becomes clear in the above description, the pre-strung array of anchors in combination with the working suture and multiple locking sutures creates a strong need for a delivery system that has components that manage the anchors and their attendant sutures or suture sections to maintain orderly implantation, use and sterility during a procedure. Further, the small size of the anchors necessitates some sort of holder or cartridge for individual anchors. Applicants disclose herein an attachable magazine and multi-cartridge assembly that integrates with the above-described delivery device. The assembly includes a cartridge for each anchor in a given array with the individual cartridges stored and managed in a cartridge magazine in a way that maintains the integrity of the array and allows the surgeon to access and use each anchor in the array sequentially.

The overall design of the anchor may include the following features. The anchor may include a distal end having an angled leading surface to encourage the anchor to begin to toggle as it exits the anchor delivery tube and nub. The anchor has a bottom side and a top side, with the bottom side being shorter than the top side due to the angled leading surface. The anchor may include a proximal end having a pair of fins on either side of a depression or dimple to receive the distal tip of the bone punch during insertion, where the dimple loosely receives the distal tip of the bone punch to allow the anchor to begin to toggle as it exits the anchor delivery tube and nub. The fins are adapted to be compressed while in the anchor delivery tube and to then open up after exiting the anchor delivery tube to discourage backing out of the anchor as it is toggled into its final position. The anchor also includes proximal and distal holes for passing the working suture therethrough, and a middle hole that allows a locking loop or cord to pass therethrough. The middle hole may include a platform that provides a surface against which the locking loop can be compressed when the free end of the locking loop is tensioned, allowing the locking loop to tighten onto and affix the working suture.

A pre-strung anchor may then be configured with the working suture passing into the proximal hole from the top of the anchor, out of the bottom side and then along the bottom side of the anchor to the distal hole. The working suture may extend up through the distal hole and exits at the top side. A locking loop extends out of the middle hole and surrounds the working suture. A pre-strung array of anchors may include a plurality of anchors disposed along a single working suture, with each anchor having its own locking loop. Alternatively, a pre-string array of anchors may include a first anchor that is permanently affixed to the single working suture, and a plurality of additional anchors each disposed along the single working suture and each having its own locking loop. Each locking loop may include a free end that can be tensioned to lock the working suture of an anchor to the anchor once implanted and tensioned.

Following are a number of illustrative and non-limiting examples. The specific features identified in these examples may be studies in conjunction with the overall system and may be further understood by reference to the following detailed description and attached Figures.

A first illustrative and non-limiting example takes the form of an assembly for locking a slidable working suture when tensioned in a suture anchor during tissue fixation to bone comprising: an anchor body having at least one suture receiving passage therethrough and a second passage therethrough; a working suture passing through the suture receiving passage wherein the working suture flosses through the suture receiving passage when tension is applied to the working suture; a locking cord extending through the second passage, the locking cord having a collapsible loop extending out the second passage and encircling a portion of the working suture, wherein the collapsible loop is configured to collapse and thereby apply force to the working suture to lock the working suture in a fixed position relative to the anchor body.

Additionally or alternatively, the locking cord comprises a suture having at least a slidable knot tied therein to form the collapsible loop to allow collapsing of the loop when a tightening leg through the second passage is tensioned.

Additionally or alternatively, the second passage has an upper portion for receiving the slidable knot at least partially therein that terminates in a platform within the second passage that does not allow passage of the slidable knot.

Additionally or alternatively, the locking loop includes first and second legs, and the second passage includes a lower portion having an oval shape for allowing both legs of the locking loop to pass therethrough side by side and out the passage.

Additionally or alternatively, the slidable knot is at least a 4-throw uni knot.

Additionally or alternatively, the second passage oval portion is sized to allow movement of at least a portion of the working suture to be pulled therein in response to tension on the locking cord.

Additionally or alternatively, the working suture is a braided multistrand suture having a compressible cross-sectional area that reduces by at least about 25% when the locking loop is tightened during use.

Additionally or alternatively, the working suture is a round No. 2 suture.

Another illustrative and non-limiting example takes the form of a plurality of assemblies for locking a tensioned suture on each of a plurality of suture anchors in a continuous single suture pre-strung chain of suture anchors for affixing tissue to bone comprising: a plurality of anchor bodies, each anchor body having at least one suture receiving passage and a second passage therethrough; a single working suture passing through each of the suture receiving passages of the plurality of anchor bodies, wherein the working suture flosses through each suture receiving passage when tension is applied to the working suture; a plurality of locking cords, a single separate locking cord extending through the second passage of each of the anchor bodies, the locking cord having a collapsible locking loop extending out the second passage and encircling a portion of the working suture, wherein collapsing the locking loop fixes the working suture relative to the anchor body.

Additionally or alternatively, each of the locking cords comprise a suture having at least a slidable knot tied therein to form the locking loop to allow collapsing of the locking loop when a tightening leg through the second passage is tensioned.

Additionally or alternatively, each of the second passages have an upper portion for receiving the slidable knot at least partially therein that terminates in a platform within the second passage that does not allow passage of the slidable knot.

Additionally or alternatively, each locking loop includes first and second legs, and each of the second passages include a lower portion having an oval shape for allowing both legs of the locking loop to pass therethrough side by side and out the passage.

Additionally or alternatively, the slidable knot is at least a 4-throw uni knot.

Additionally or alternatively, each of the second passage oval portions are sized to allow movement of at least a portion of the working suture to be pulled therein in response to tension on the locking cord.

Additionally or alternatively, the working suture is a braided multistrand suture having a compressible cross-sectional area that reduces by at least about 25% when the locking loop is tightened during use.

Additionally or alternatively, the working suture is a round No. 2 suture.

Another illustrative and non-limiting example takes the form of a method for locking a working suture in a fixed position relative to a suture anchor through which the working suture is tensioned during tissue fixation to bone, the method comprising the steps of: providing an anchor body having at least one suture receiving passage therethrough with a working suture passing through the at least one suture receiving passage wherein the working suture flosses through the passage when tension is applied to the working suture and at least one second passage through the anchor body; the anchor body further having a locking cord extending through the second passage, the locking cord having a collapsible locking loop extending out the second passage and encircling a portion of the working suture; tensioning the working suture by applying force; and, collapsing the locking loop to lock the working suture in place.

Additionally or alternatively, a plurality of anchors are pre-strung on a single working suture, each with a locking loop, and the working suture is implanted by sequentially performing the tensioning and collapsing steps for the plurality of anchors to create a plurality of tensioned suture bridges between anchor bodies.

Additionally or alternatively, the collapsible locking loop is formed from a suture having a slidable knot formed therein.

Additionally or alternatively, the slidable knot is at least a 4-throw uni knot.

Another illustrative, non-limiting example takes the form of a pre-strung toggle anchor comprising a toggle body having a proximal end and a distal end with at least first and second bores extending therethrough, a working suture passing through the first bore, and a locking cord having a loop at one end passing around working suture and extending out of a first end of the second bore, and a free tail extending out of a second end of the second bore, the locking cord being configured with a preferential point of weakness and having a sliding knot thereon, the preferential point of weakness configured to break the free tail of the locking cord when pulled with a breaking force.

Additionally or alternatively, the locking cord is configured to tighten about the working suture to lock the working suture to the toggle body when a pulling force less than the breaking force is applied to the free tail.

Additionally or alternatively, the toggle body comprises a third bore, and has a top surface and a bottom surface, each bore extending from the top surface to the bottom surface, wherein the working suture enters the first bore at the top surface, exits the first bore at the bottom surface, passes along the bottom surface past the second bore and to the third bore, enters the second bore at the bottom surface and extends through the first bore at the top surface, and the locking cord is configured with the locking loop extending out the second bore along the bottom surface of the toggle body and the free tail extending out of the second bore at the top surface of the toggle body.

Additionally or alternatively, the locking loop is defined by a sliding knot adapted to reside in the second bore.

Additionally or alternatively the preferential point of weakness of the locking cord is defined by a nick in the locking cord.

Additionally or alternatively the preferential point of weakness of the locking cord is defined at a break knot in the locking cord.

Another illustrative, non-limiting example takes the form of a method of creating a stitch between two anchors placed in a bone, the method comprising implanting a first anchor having a working suture extending therefrom, placing a second anchor threaded onto the working suture in a bone hole, the second anchor comprising first and second bores, the working suture extending through a first of the bores and a locking cord extending through the second of the bores, the locking cord having a collapsible locking loop surrounding the working suture, pulling on the working suture after placing the second anchor in the bone hole to tighten the working suture between the first and second anchors, and pulling on the locking cord to collapse the locking loop onto the working suture.

Additionally or alternatively, the locking cord includes a preferential point of weakness, and the method comprises, after pulling on the locking cord to collapse the locking loop onto the working suture, pulling further on the locking cord to break the locking cord at the preferential point of weakness. Additionally or alternatively the preferential point of weakness of the locking cord is defined by a nick in the locking cord. Additionally or alternatively the preferential point of weakness of the locking cord is defined at a break knot in the locking cord. Additionally or alternatively, the locking loop is defined by a sliding knot adapted to reside in the second bore.

Additionally or alternatively, the method also includes, after placing the second anchor in the bone hole, pulling on the working suture to toggle the second anchor and thereby affix the second anchor in the bone hole. Additionally or alternatively, the step of pulling on the working suture to toggle the second anchor is performed before pulling on the working suture to tighten the working suture between the first and second anchors.

Additionally or alternatively, the second anchor comprises a third bore and the working suture passes through the third bore such that a portion of the working suture extends alongside the second anchor between the first and third bores, past the second bore where the locking loop is located. Additionally or alternatively, the step of pulling on the locking cord to collapse the locking loop onto the working suture comprises pulling a portion of the workings suture into the second bore.

This overview is intended to introduce the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 3D-3F are close up views of the distal end of the anchor delivery device corresponding to FIGS. 3A-3C;

FIGS. 3J-3N are partial cut-away views illustrating the interaction of internal components of the anchor delivery device;

FIG. 3O is a partial cut-away view of the anchor delivery device in another configuration;

DETAILED DESCRIPTION

The present invention includes multiple components, devices and methods to create and use an overall system for reattaching soft tissue to bone. It is particularly useful to create a robust repair of torn tendons, such as the supraspinatus tendon, in an arthroscopic rotator cuff repair. The implants and delivery devices make possible a faster, easier and lower failure rate anatomical repair. The tendon is securely attached and held with adequate force to its original footprint with very little creep during movement of the joint. This decreases a patient's time in a sling, increases the rate of healing reattachment of tendon to bone and allows early physical therapy to maintain range of motion and strength.

The implanted array of anchors with a continuous set of anchor-to-anchor single suture stitches creates a seam-like attachment akin to a sewing machine construct. Further, the small cross-sectional size of the anchors (less than 3 mm in diameter) allows the anchors to be placed in close proximity to one another (less than about 7 mm between adjacent anchors). This creates an anchor to anchor suture stitch. Combining this concept with the disclosed anchor design allows the suture stitch to be tightened and locked individually when the adjacent suture anchors are implanted. This can be repeated many times to implant a row of anchors with continuous independently tensioned and locked stitches between adjacent anchors. Also, because the anchors are in a high-density array, the tension force components on the tensioned suture are more vertically applied to the top surface of the tendon (or other connective tissue) to thereby hold the tendon against the footprint of the bone without creep or slippage during joint movement.

FIGS. 1A-1K are a series of illustrations of exemplary toggle bodies or toggle-type anchors that can be used in a procedure for attaching tendon to bone. The illustrations also show a single working suture slidably disposed in passages through the anchor and through a locking loop. The locking loop is configured to have an open position allowing movement of the single working suture, and a closed or locked position that prevents movement of the single working suture.

Figure 1A:
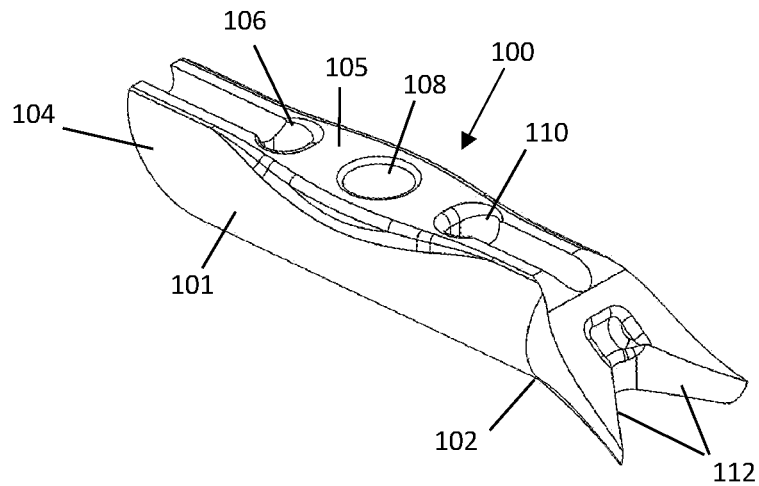
FIGS. 1A-1E are various views of a representative toggle body.

Referring to FIG. 1A, a perspective view of a representative anchor in the form of a toggle body 100 is illustrated. The toggle body 100 can be an elongate body 101 having a length defined by a proximal end 102 and a distal end 104. The elongate body 101 can be a generally cylindrical body but other shapes are possible. For example, as shown in FIG. 1A, the toggle body 100 is generally cylindrical but the top surface 105 and bottom surface 107 have flat axially-extending surfaces that allow room for sutures when the toggle body 100 is in a round delivery tube. The length of the toggle body 100 is substantially longer than the diameter thereof, allowing the toggle body 100 to be inserted lengthwise or axially into a small bone hole. Once inserted, unlike most anchors used today, the entire body is pivoted or toggled so that it stays within the bone and has substantially its entire length compressed against material inside the bone. That is, the longitudinal axis of the toggle body 100 is rotated or pivoted from the direction used to insert through the bone hole, thereby preventing removal. This approach means that removal would require the anchor itself to fail, rather than simply being released from surrounding tissue, and provides high pullout strength (greater than 600 N before anchor failure when implanted in the array disclosed herein) from an anchor requiring a very small insertion hole (less than about 3 mm). As previously stated and described in detail below, small insertion holes allow much closer placement of anchors in a high-density array.

The toggle body 100, can have a length of about 6 mm to about 10 mm in some embodiments. This length gives adequate strength while leaving enough room inside the bone for the high number of anchors implanted. The toggle bodies are preferably molded or machined from a polymeric material, preferably a high tensile strength material such a poly-ether-ether ketone (PEEK) which is highly biocompatible. In applications where MRI imaging would not be an issue, metal can be utilized in part or all of the toggle body.

Figure 1B:
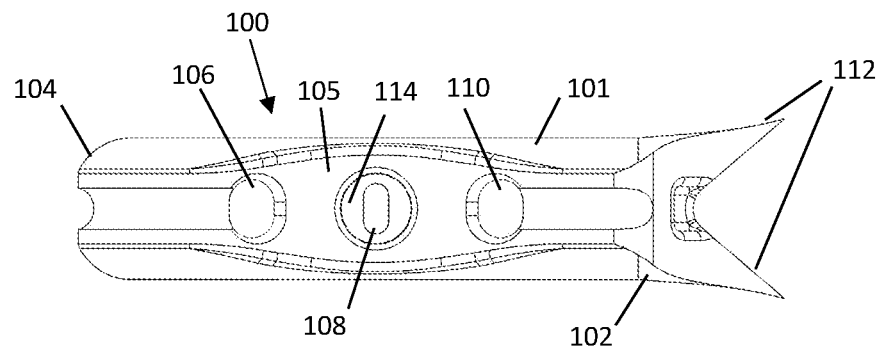

Referring now also to FIGS. 1B (top view) and 1C (bottom view), it can be seen that the toggle body 100 can include a number of holes or passages through the cross section of the toggle body 100. As illustrated, the toggle body 100 has a proximal bore or passage 110, a middle passage 108 and a distal passage 106. The passages 106, 108, 110 extend from the top surface 105 to the bottom surface 107 such that the passages 106, 108, 110 extend through the cross section of the elongate body 101. In other embodiments, the toggle body may have fewer or more bores or passages, such as having a single bore, two bores, or more than three bores. In the illustrated embodiment, the proximal passage 110 and distal passage 106 receive a portion of a common working suture slidable with respect to the toggle body 100 during use. The middle passage 108 receives a locking suture which is independent for each anchor used in an array of anchors.

The distal end 104 of the toggle body 100 has an angled surface. As shown, the angled surface creates a longer upper longitudinal surface 105 than lower longitudinal surface 107. In other words, the upper surface projects a greater distance distally than the lower surface. This is useful during insertion of the toggle body 100 because the projecting distal surface plows into cancellous spongy bone when implanted to initiate at least partial rotation of the toggle body during insertion. Keeping in mind that the present toggle bodies 100 are preferably implanted through the tendon, it is important that the toggle body 100 toggle every time or it may pull out of the bone hole under tension yet not be visible as it will be under the tendon.

The proximal end 102 of the toggle body 100 can include one or more projecting fins 112. The illustrated embodiment includes two fins 112. Each fin 112 projects outward and proximally. Further, in some embodiments, as depicted, the fins 112 project downward as they extend proximally. The function of the fins 112 is best understood with reference to FIGS. 1D and 1E which are distal and proximal end views of the toggle body 100, respectively. A reference circle 113 is included which indicates the general maximum cross section or diameter of the elongate body 101. The bone hole in which the implant will be placed is sized to closely match this dimension, as is the inner diameter of a delivery tube used to deliver the implant. In contrast, as shown, the fins 112 each project laterally beyond the outer cross section or diameter of the elongate body. During insertion the fins 112 flex inward under compressive force due to contact with the inner diameter of a delivery tube to fit in the bone hole.

Once delivered and released from compressive forces of the delivery tube, the fins 112 relax to a size greater than the bone hole. In some preferred embodiments, each fin tip extends about an additional 0.5 mm beyond the size of the bone hole where that feature is inserted. Such fin tips may also be described as extending about 0.5 mm beyond the maximum outer diameter of the rest of the anchor body, for example, in the range of 0.4 mm to 0.7 mm. This feature provides an added safeguard against the toggle body 100 backing out of the bone hole under tension if the toggle body 100 has not adequately toggled. Further, the fins 112 are positioned so that tension on the toggle body 100 causes the partially toggled anchor to grab cancellous bone and further rotate the anchor.

Figure 1C:
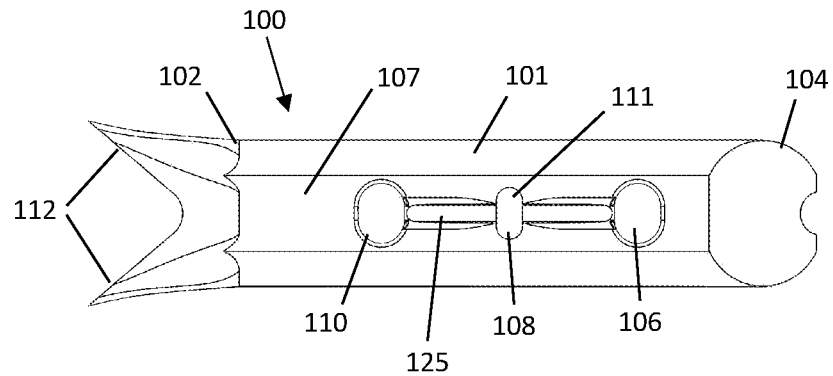
Figure 1D:
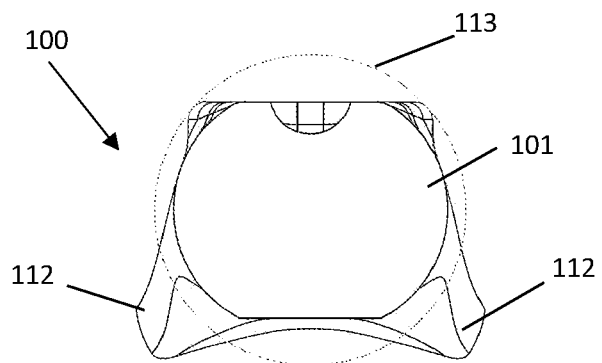
Figure 1E:
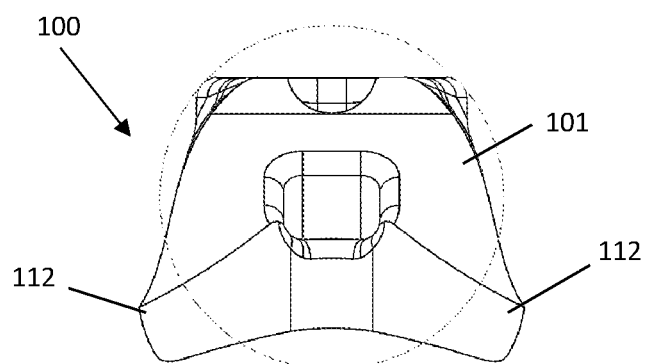
Figure 1F:
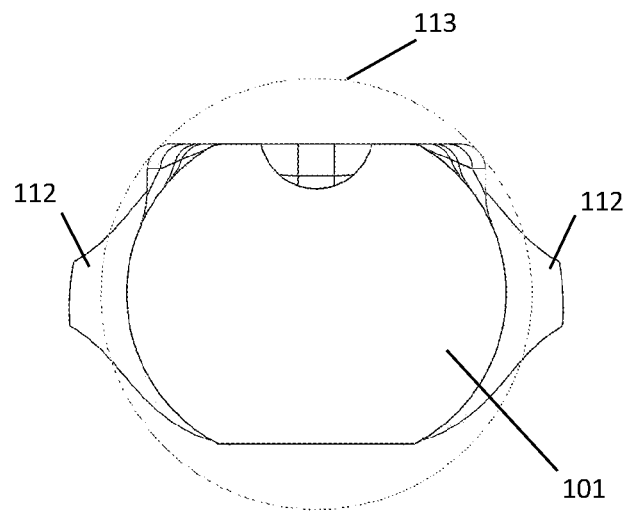
FIGS. 1F-1G are views of alternative fin orientations in a toggle body.
Figure 1G:
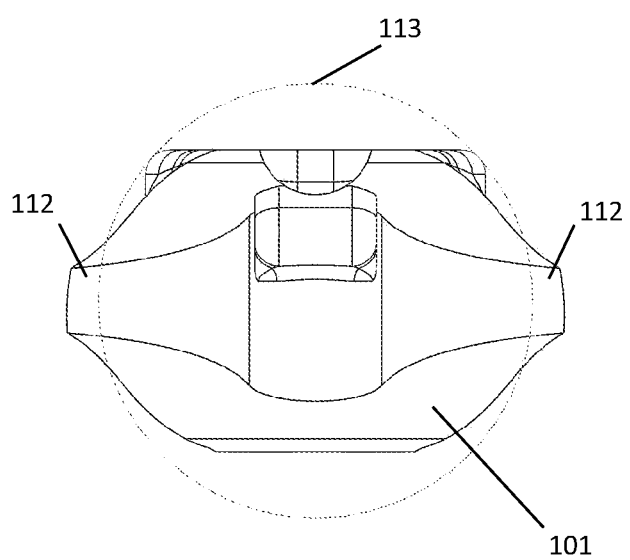

Alternative designs of the fins 112 are also depicted in FIGS. 1F and 1G. The fins 112 in these figures have alternative positions on the elongate body 101 and direction of proximal extension. The fins 112 of FIG. 1F are widest at a centrally located position to keep the anchor centered in the delivery tube since the largest dimension is horizontal at the diameter of the tube during delivery. In some examples, the fins do not provide the pullout strength necessary for the implanted anchor to reattach the tendon. As previously stated, in preferred examples, each anchor toggles so that the full length of the anchor is pressed against interior bone structure to provide adequate pull out strength.

The top and bottom views of FIGS. 1B and 1C show details of the proximal 110, middle 108 and distal 106 passages. In particular, the middle hole has a platform 114 formed within the elongate body 101, part way through the cross section. That is, in this example, the middle passage 108 has a change in size or shape partway along its length, to define a platform 114. From the bottom view, it can be seen that the middle passage 108 continues from the platform 114 with a slotted or oval shape or portion 111, while having a circular profile from the top view. The function of these passages is detailed in the cross-section perspective views of FIGS. 1H and 1I wherein representative cords or sutures 115, 116 have been pre-strung on the toggle body 100.

Figure 1H:
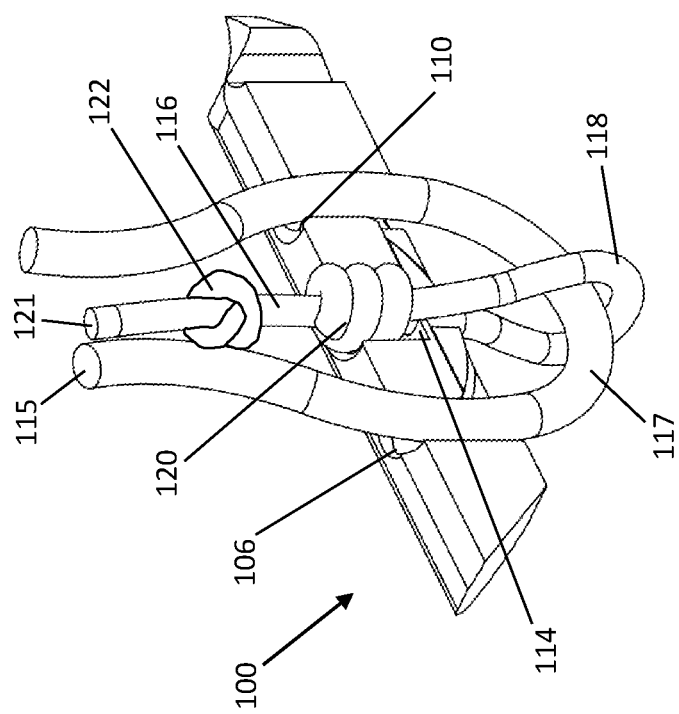
FIG. 1H is partial cut-away view of a toggle body with a working suture and locking suture in an open position illustrated.

First, there is a single suture, called herein the working suture 115 that extends into the proximal passage 110 from the top surface, and extends out at the bottom surface. The working suture 115 then extends up through the distal passage 106 from the bottom surface and out through the top surface. This leaves a section 117 of the working suture 115 extending past or adjacent the middle passage 108 along the bottom surface. The working suture 115 can be flossed or is slidable through the distal 106 and proximal passage 110, meaning the toggle body 100 can slide on the working suture 115 when tension is applied. Second there is a locking loop 118 that encircles a portion of the section 117 of the working suture 115 extending adjacent the outer surface of the toggle body 100 between the proximal 110 and distal 106 passages. The locking loop 118 has a first open position as depicted in FIG. 1H wherein the working suture 115 is free to slide through the locking loop 118 and a second closed position depicted in FIG. 1I wherein the locking loop 118 engages the section 117 and prevents it from sliding within the locking loop 118.

Several examples refer to a suture, cord, or thread, which can be used as the working suture 115 or in the locking loop 118. These elements may be, for example, made of natural material such as silk and/or synthetic materials such as polyglycolic acid, polylactic acid, and polydioxanone, each of which are known for use as absorbable sutures, and/or nylon and polypropylene, which are typically non-absorbable. Various coatings, including antimicrobial, anti-wicking or lubricious coatings may be applied as well. More broadly, these elements 115, 118 may include any item that can be used to couple together objects in a surgical environment, such as any sufficiently biocompatible metal, natural material, plastic or other artificial material adapted for use in a surgical procedure. Monofilaments or more complex structures including braids, weaves, windings, twisted threads, coated or multilayer member, etc. may be used.

In the embodiment depicted, the locking loop 118 extends from the bottom surface of the toggle body 100 through the middle passage 108. The locking loop 118 includes a cord or suture having at least a slidable knot 120 tied therein to allow collapsing of the locking loop 118 when a free end or proximal end 121 of the suture lock 116 extending through the middle passage 108 is tensioned. As shown, the upper portion of the middle passage 108 is sized to receive at least a portion of the slidable knot 120 therein. The slidable knot 120 then contacts the surface of the platform 114 which does not allow the knot to pass through towards the bottom opening. The lower oval portion 113 of the middle passage 108 is a slot or oval which allows both legs of the locking loop 118 to pass therethrough, preferable side by side in the slot direction. The interaction of these components locks the working suture 115 with respect to the toggle body 100.

Figure 1I:
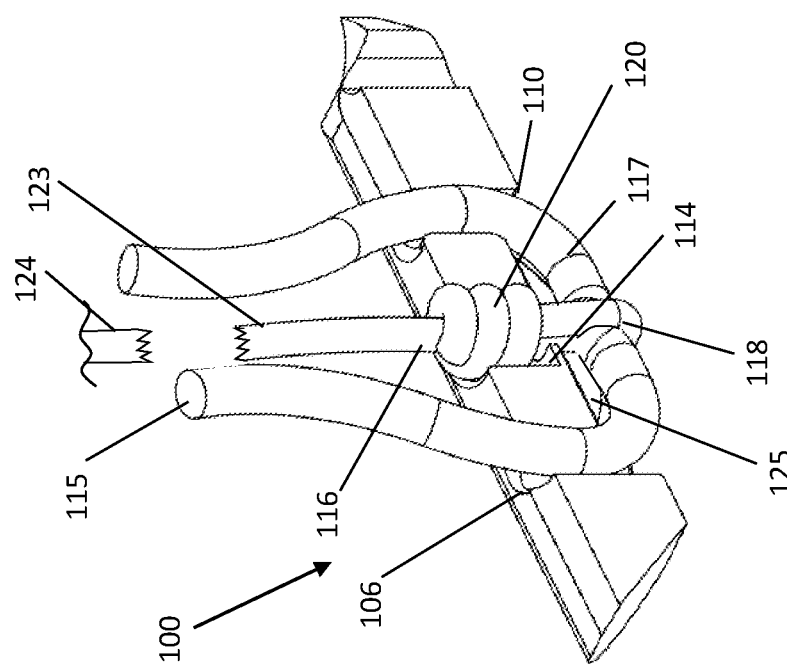
FIG. 1I is partial cut-away view of the toggle body of FIG. 1H having a working suture and locking suture in a closed position illustrated.

As shown, especially seen in FIGS. 1C and 1I, the bottom of the toggle body 100 includes a channel 125 formed in the bottom surface 107 between the proximal 110 and distal 106 passage. When the working suture 115 is tensioned, it is pulled up into this channel 125 which is sized to make the suture less able to floss or move therethrough by increasing frictional resistance to such movement, but does not lock the suture. Further, the working suture then has two near 90-degree angle turns at the bottom openings of the distal 106 and proximal 110 passage which also make it more difficult to floss, but do not lock the working suture 115. The locking loop 118 closing around the working suture 115 and pulling it toward and at least partially into the slot or oval portion 113 is the structure that locks the suture so that cumulative friction prevents slippage of the working suture 115.

In the illustrative example shown in FIGS. 1H to 1K, the free end 121 of the suture lock 116 is configured to break away from the locking loop 118 proximal of the sliding knot 120. A break knot is illustrated at 122 and is one example of a way of introducing weakness in the suture lock. The break knot 122 is located a distance above the sliding knot 120, sufficient that when the suture lock 116 breaks away, the sliding knot 120 remains intact and secure; for example, 3 to 10 mm proximal of the sliding knot, or more or less. Rather than a break knot 122, a nick or other point of weakness may be imparted at the desired or preferential point of failure in the suture lock 116.

Figure 1J:
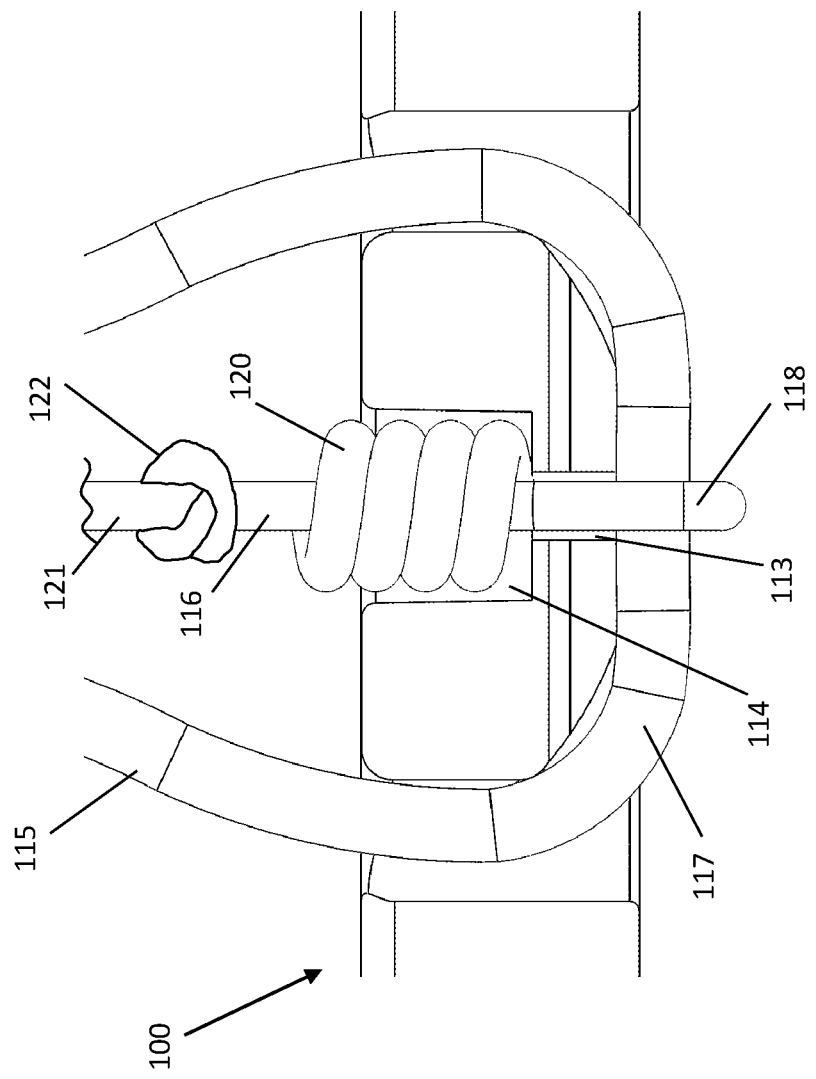
FIG. 1J is a schematic illustration of the interaction between the locking suture and the working suture.
Figure 1K:
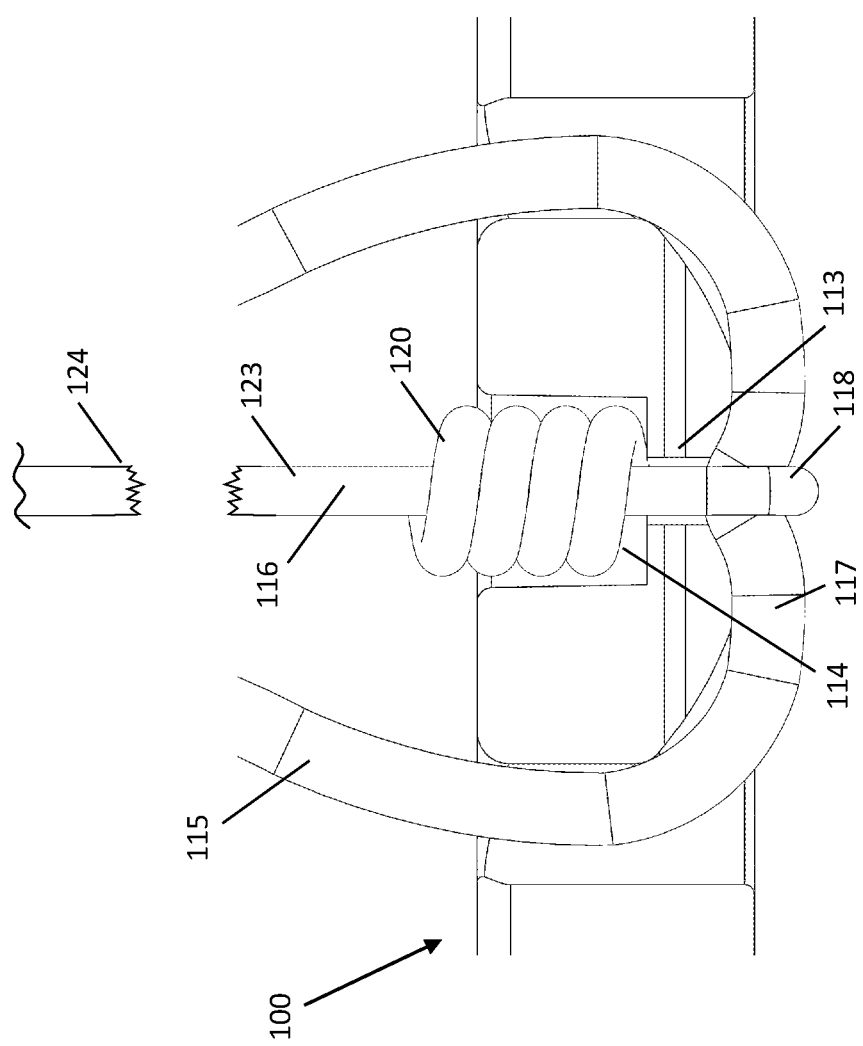
FIG. 1K is a schematic illustration of an alternative interaction between the locking suture and the working suture.

FIGS. 1J and 1K depict the way in which the locking loop 118 pulls the section 117 of the working suture 115 into the oval portion 113 in two different embodiments. The degree to which the section 117 of the working suture 115 enters the slot 113 will be dependent upon how tight the loop is closed, the size of the locking suture and the size of the slotted opening. In preferred embodiments, at least a portion of the cross section of the working suture 115 is pulled into the slot so that the edge surfaces of the slot walls provide significant friction and aid in locking. In another example, the preferential point of failure is designed to allow the locking loop 118 to be drawn into the slot before the failure occurs.

The locking loop 118 in combination with the design of the middle passage 108 is an assembly for locking a slidable working suture 115 when tensioned in a suture toggle body 100 during tissue fixation to bone. The locking loop 118 encircles a portion of the working suture 115, wherein collapsing the locking loop 118 compresses the cross section of the working suture 115 to lock the working suture 115 when tensioned. The suture lock 116 is preferably formed of a suture having at least a slidable knot 120 tied therein to form the loop 118 to allow collapsing of the loop 118 when a tightening leg 121 through the second passage 108 is tensioned. The second passage 108 has an upper portion for receiving the slidable knot 120 at least partially therein that terminates in a platform 114 within the toggle body 100 that does not allow passage of the slidable knot. The second passage includes a lower portion having an oval shape for allowing both legs of the locking loop to pass therethrough side by side and out the passage. A particularly preferred knot is a 4-throw uni knot. However, other slidable knots 120 may be used, as desired. Further, the second passage oval portion is sized to allow movement of at least a portion of the working suture 115 to be pulled therein in response to tension on the locking cord. The working suture 115 is preferably a braided multistrand suture having a compressible cross-sectional area that reduces by at least about 25% when the locking loop is tightened during use. The working suture 115 can be a round and/or braided No. 2 suture in some embodiments. Other suture sizes and types may be used.

As also shown in FIGS. 1I and 1K, after the sliding knot 120 is tightened, and the working suture is drawn at least partly into the slot, the preferential point of failure in the locking loop 116 (such as the break knot or nick described above) breaks, leaving free tail at 123 on the locking loop, a distance above the sliding knot, while the rest of the proximal portion of the suture lock 124 can be discarded. In some examples, a more proximal portion of the suture lock is secured to a cartridge, so that a physician may cause the suture lock to break as shown by pulling on the cartridge itself, as further described below. In an example, the preferential point of failure is designed to allow tightening of the locking loop 118 onto the working suture 115 before the failure occurs. For example, the locking loop and the preferential point of failure may be configured for breaking under a pull strength in the range of 3-10 pounds of force, more preferably, 5-7 pounds of force, or more or less as desired. The pull strength needed to tighten the locking loop 118 onto the working suture may be less than the pull strength needed for breaking the preferential point of failure in some examples by, for example, an amount in the range of 0.5 to 3 pounds, or 0.75 to 2 pounds, or about 1 pound.

Figure 2A:
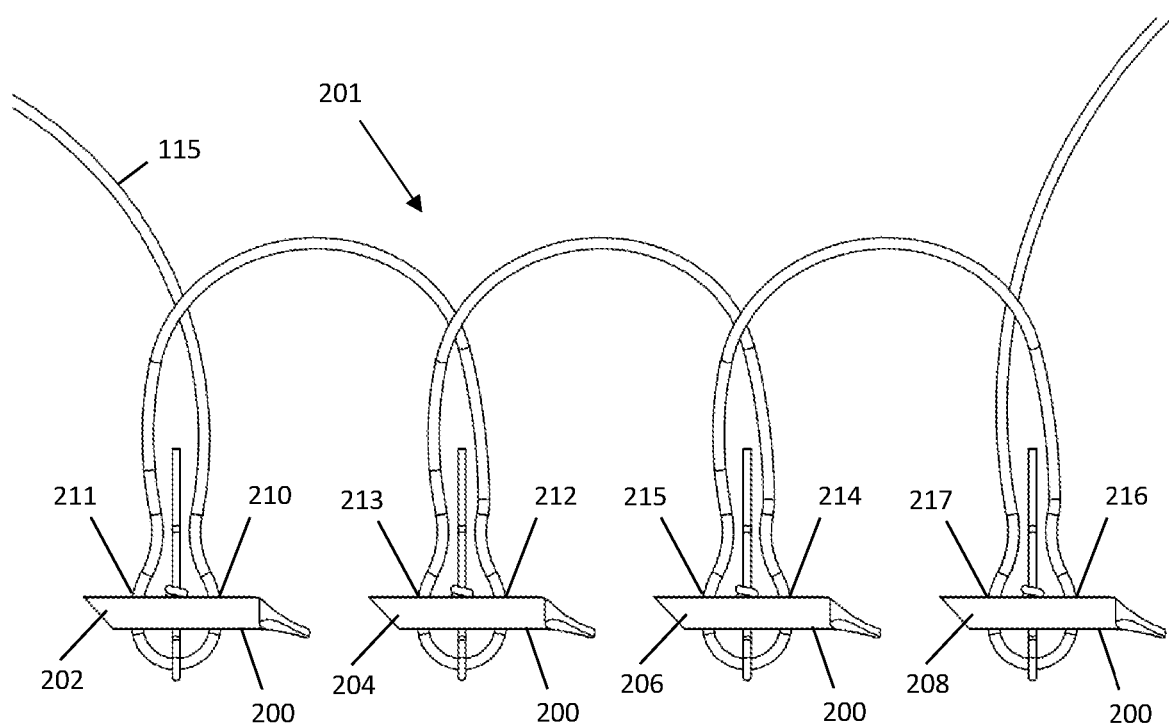
FIG. 2A is an illustration of a pre-threaded array of toggle type anchors.

In some preferred embodiments, the above-described anchor does not function alone. Instead it is part of a pre-strung array of anchors having a common serially disposed working suture 115 therethrough. FIG. 2A illustrates a pre-strung array 201. Each anchor 200 can be implanted sequentially within the array, then the working suture section extending from the just implanted anchor to the just previously implanted anchor can be tensioned, then locked at the just implanted anchor so that a suture stitch between the two anchors provides force against the tendon to hold it in place much like a single sewn stitch. With the array, multiple continuous stitches can be formed similar to a sewn seam.

In FIG. 2A a pre-strung array 201 of individual anchors 200 is depicted. The anchors 200 may be similar in form and function to the anchor 100 described herein. The shown array has four anchors 200 as a representative chain. It is believed chains of 4 to 12 anchors would be useful in tendon repair procedures such as rotator cuff repair. One particular embodiment includes 8 anchors in an array. As depicted in FIG. 2A, the way in which the working suture 115 is pre-threaded through the series of anchors 200 is important to assure that they will toggle as desired and tension to form the stitch when the suture is tightened. The illustration shows the first anchor 202 to be implanted followed by the second anchor 204, then the third anchor 206 and finally the fourth anchor 208. With this order of implantation understood, the working suture 115 has been pre-threaded down through the top of the proximal hole 210 and back up through the distal hole 211 of the first anchor 202. The working suture 115 then continues to the second anchor 204 where it is threaded down through the proximal hole 212 and back up through the distal hole 213 of the second anchor 204. The working suture 115 then continues to the third anchor 206 where it enters the top of the proximal hole 214 and back up the distal hole 215 of the third anchor 206. The working suture then continues to the fourth anchor 208 where it enters the top of the proximal hole 216 and passes up through the bottom of distal hole 217 of the fourth anchor 208. If the array were more than four anchors, the pre-threading would continue as described for each subsequent anchor.

Figure 2B:
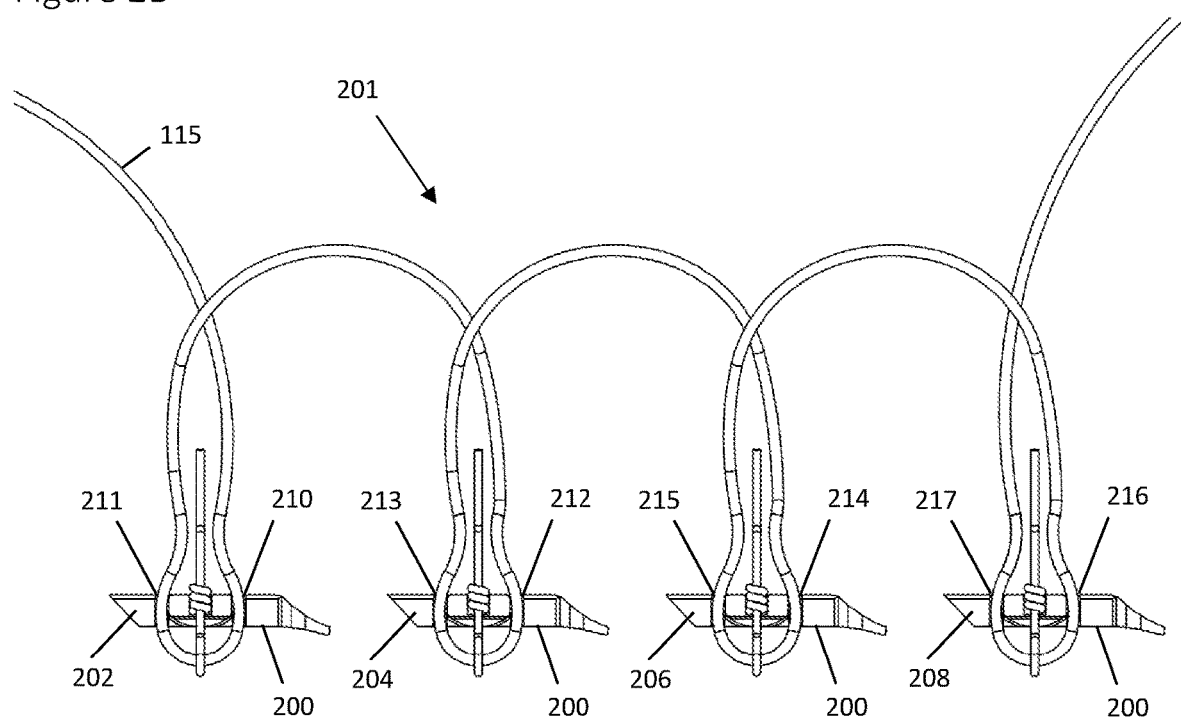
FIG. 2B is an alternative view of FIG. 3A showing the toggle anchors in cross section to illustrate the threading route of the sutures.

FIG. 2B is a cross sectional view of the array of FIG. 2A which more clearly shows the threading of the working suture 115 within the anchors 200 in the array 201. The way in which the locking suture 116 is disposed in the middle passage is also shown for each anchor 200 as described above with each locking loop 118 independent for each anchor. The locking suture 116 can have a preferential point of failure so that it can be tightened then broken off above the slidable knot. This can be accomplished by tying a break knot, or making a nick in, in the free tail of the locking loop just above the slidable knot, as further illustrated in FIGS. 1H to 1K, above. In some preferred embodiments the slidable knot is a 4-throw uni knot and the break knot is in the free tail just above the uni knot. The suture lock may be designed to break at a desired tension with the slidable knot in place sufficient to lock the working suture.

To create an implanted serial array of tensioned and independently locked anchor to anchor suture stitches for attaching a tendon to bone, a surgeon would begin with the pre-strung array 201 described in FIGS. 2A and 2B. The first anchor 202 would be implanted through the tendon into a formed bone hole and the working suture locked. The second anchor 204 would then be implanted in close proximity to the first anchor 202, preferably less than 7 mm away. The second anchor is toggled and the working suture tensioned at the same time by pulling on the working suture 115 that exits the distal hole 213 of the second anchor 204. Tension at this location not only toggles the second anchor 204 but also tightens the working suture 115 going back to the first anchor 202 to form the tensioned stitch holding the tendon against the footprint. The second anchor 204 is then locked so that the stitch remains tensioned and is isolated or independent of other stitches. The process is repeated for the third anchor 206 and fourth anchor 208 or more. In one preferred array, eight anchors are implanted and 7 tensioned and locked stitches in a continuous row are formed. Further, in a rotator cuff repair, multiple arrays can be implanted such as one array extending across the tendon in the medial portion of the footprint and a second array more lateral to the medial position.

Figure 3A:
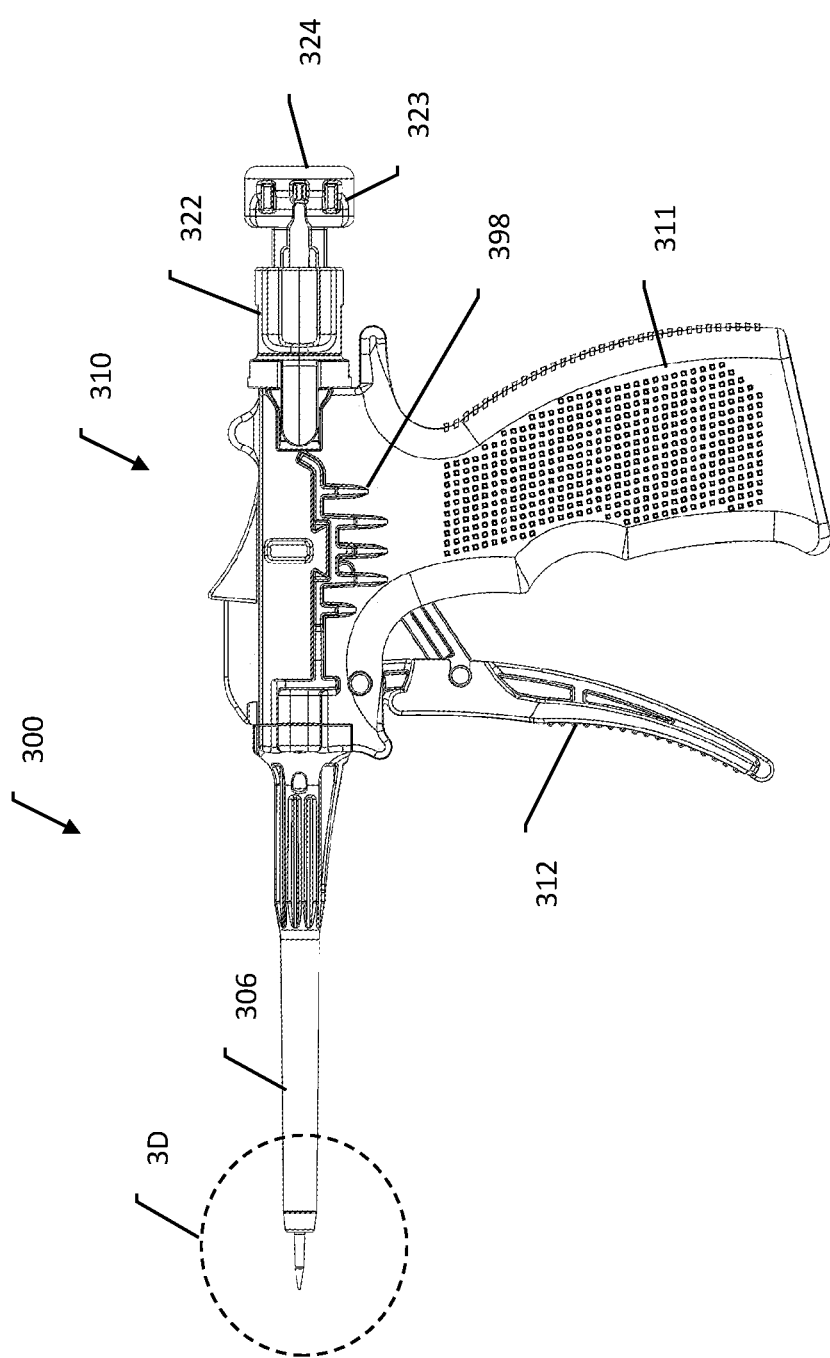
FIGS. 3A-3C are perspective views of an example anchor delivery device in several configurations.

One preferred anchor delivery device 300 for transtendinous implantation of individual anchors in an array is depicted in FIG. 3A. The delivery device 300 is particularly useful to implant anchors disclosed herein and detailed below with respect to FIGS. 1A-1K and the disclosed array in FIGS. 2A-2B.

Figure 3B:
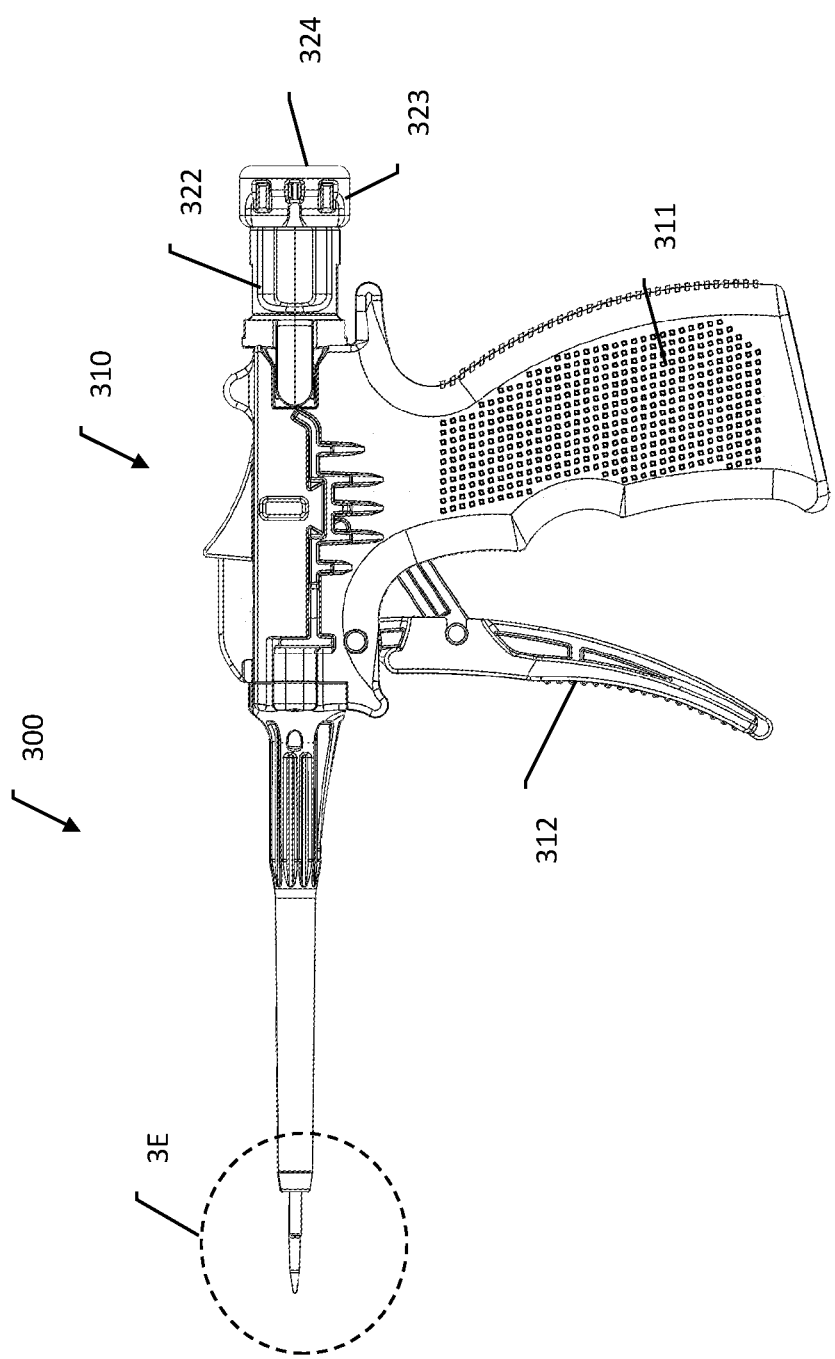
Figure 3C:
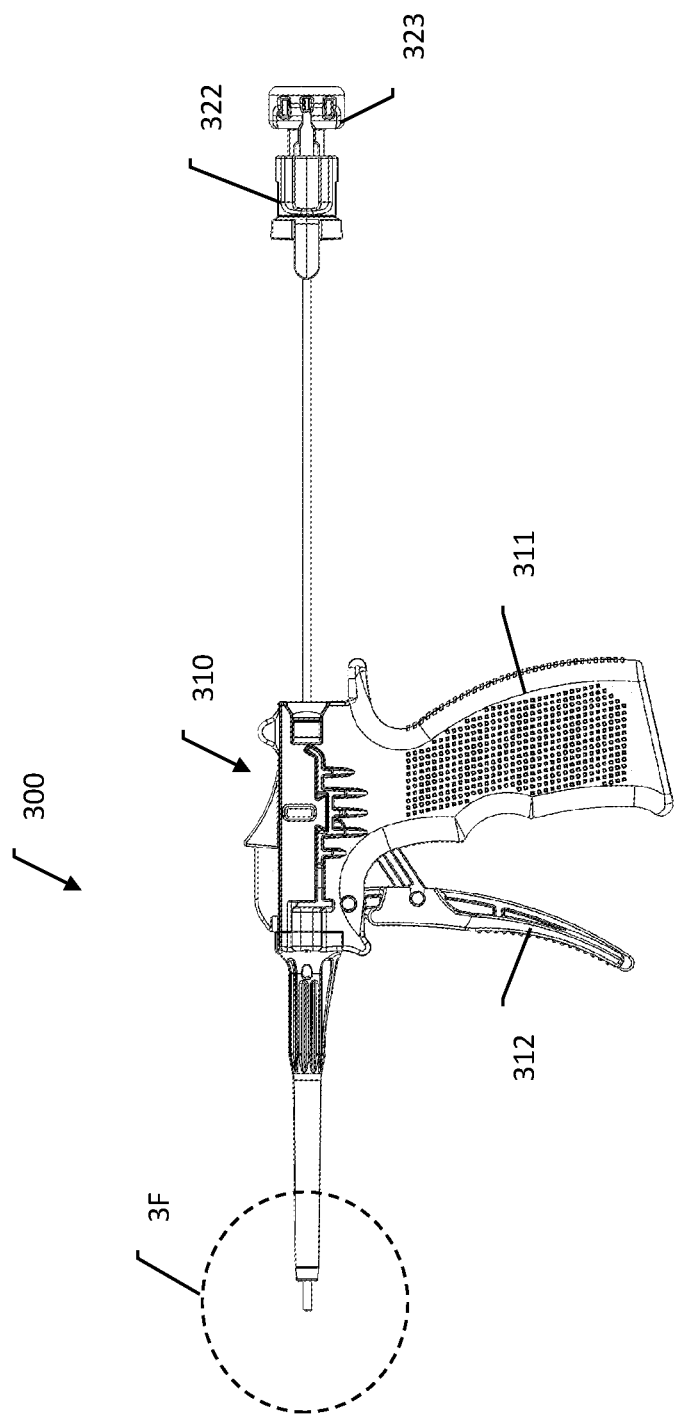

FIGS. 3A-3C are perspective views of an example anchor delivery device in several configurations, and FIGS. 3D-3F are close up views of the distal end of the anchor delivery device corresponding to FIGS. 3A-3C. Starting with FIG. 3A, the delivery device 300 can be a gun-like component that has a proximal housing 310 that includes a pistol grip type handle 311 and trigger 312 that moves from a spring retained released position to an engaged position upon squeezing and holding the trigger (as further illustrated below). The trigger 312 is linked to moveable internal features within the proximal housing 310 to provide desired functions during implantation described below. The delivery device 300 includes an elongate tube 306 extending distally from the proximal housing 310. As shown in the close-up view of FIG. 3D, the elongate tube 306 includes a longitudinal slot 307 over its length for receiving sutures therethrough as anchors are passed through the central lumen of the tube.

FIG. 3A also shows that the proximal housing 310 is associated with a bone punch having a distal punch head 322 and a proximal punch head 323. The proximal punch head 323 has a tapping surface 324 at its proximal side. Combined elements 322 and 323 form a punch head assembly. As illustrated in FIG. 3D (which corresponds to the configuration of FIG. 3A), the bone punch also includes a punch pin 320 having a tapered point 321 adapted for probing through the tendon and/or grabbing the tendon to aid positioning. Positioning may include positioning the tendon in its original footprint, for tendons that are detached. In some examples, positioning as a separate step may be omitted or limited, such as when repairing a partial tear, such as a partial thickness articular side tear or combination of full thickness and articular partial thickness tears. A tendon can be considered positioned at a location for securing to bone either by virtue of having placed a fully torn or detached tendon at a location, such as its original footprint, where it can be re-attached, or, with a partial tear, when the tendon is located where a physician desired to have it when applying anchors to repair or otherwise address the partial tear.

Figure 4A:
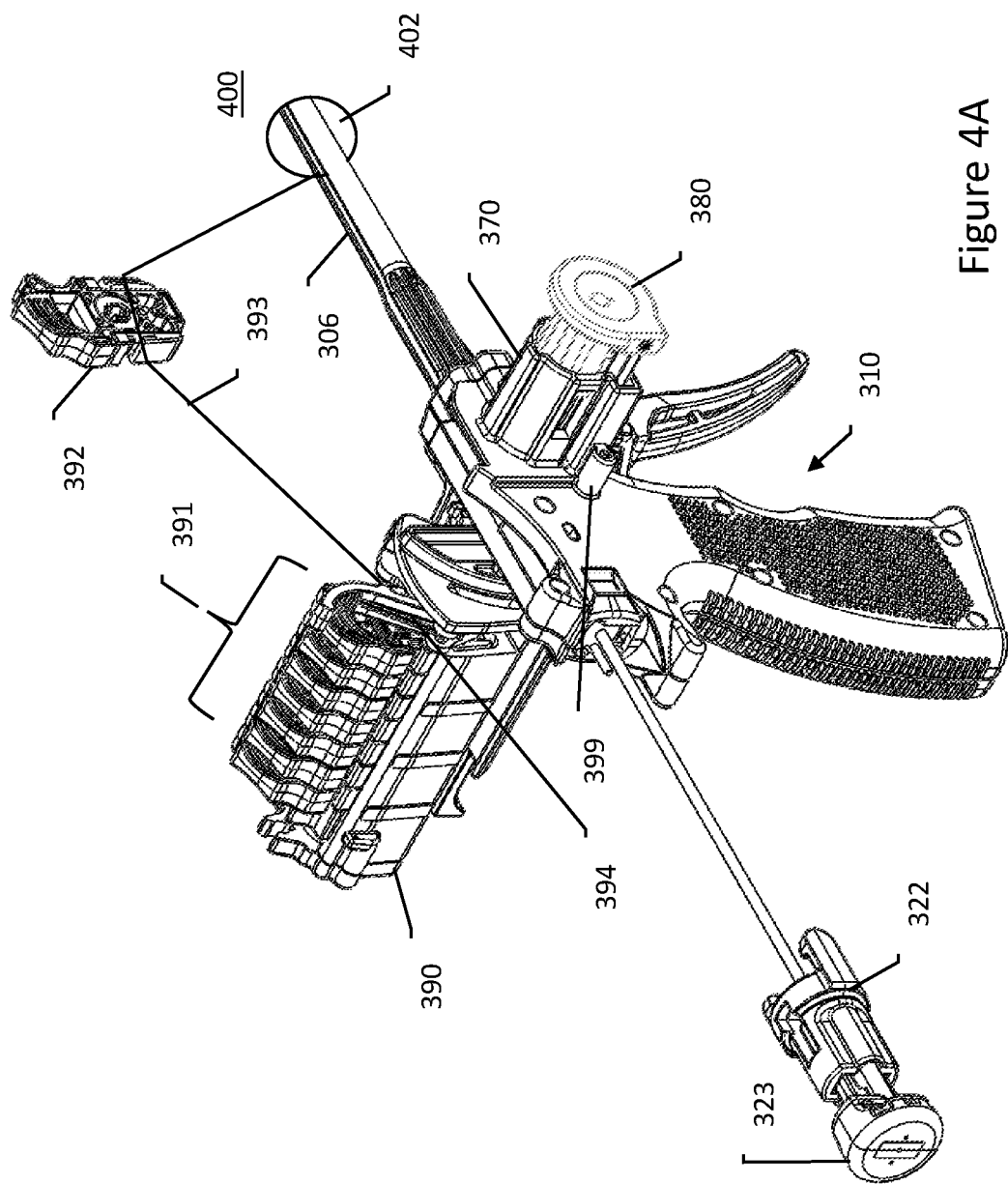
FIGS. 4A-4D illustrate features of a plunger for securing cartridges to the anchor delivery device.

The punch pin 320 and tip are configured for being pounded into bone to create a bone hole; the tapered point 321 is also used in some methods disclosed herein to engage and push against the proximal end of an anchor. The punch pin 320 extends through the proximal housing 310 and the elongate tube 306. The punch pin 320 is affixed to the proximal punch head 323 and is slidable within the distal punch head 322. The distal punch head 322 snap latches to the proximal housing 310 of the delivery device. The proximal punch head 323 and distal punch head 322 are connected by a spring-loaded mechanism that holds the punch pin 320 in a fully extended position when the proximal punch head 323 is pushed against the distal punch head 322 and latched. When the proximal punch head 323 is released from close connection with the distal punch head 322, the spring loading causes the punch pin 320 to withdraw proximally to a partially retracted position with only a short distal portion of the punch pin 320 extending beyond the elongate tube 306 for use in probing a potential implant site. Such a configuration of the implant tool is shown in FIGS. 3A and 3D, where the punch pin 320 is the only piece extending from the distal tip of the elongate tube 306, the distal punch head 322 is latched to the proximal housing 310, and the proximal punch head 323 is not latched to the distal punch head 322. Also included on the proximal housing 310 is a receiver 398 for receiving a magazine that carries cartridges which hold individual anchors of the array to be implanted, as is illustrated in FIG. 4A, below.

FIG. 3B and corresponding FIG. 3E show another configuration of the delivery device 300. Starting with FIG. 3B, it can be seen that the trigger 312 remains in a relaxed position and is not depressed (similarly to FIG. 3A). The proximal punch head 323 is now latched to the distal punch head 322. Latching together of the punch head causes the distal end of the punch pin 320 to extend further from the distal end of the elongate tube 306, as shown in FIG. 3E. Now an additional element can be seen, in that the elongate tube 306 has an anchor delivery tube 330 disposed therein. The action of latching together the proximal punch head 323 with the distal punch head 322 advances the anchor delivery tube 330 distally, and forces a distal portion of the anchor delivery tube 330 past the distal end of the elongate tube 306. The anchor delivery tube 330 also has a longitudinal slot 331 aligned with the longitudinal slot 307 of the elongate tube for passing a suture therethrough. With the anchor delivery device 300 configured as shown in FIGS. 3B and 3E, the device is ready for a surgeon to pound or tap the tapping surface 324, such as with a surgical mallet, to force the punch pin 320 and its tip 321 into bone to create a bone hole.

FIGS. 3C and 3F show a next configuration of the delivery device. Here, the distal punch head 322 is no longer engaged with the proximal housing 310, and the proximal and distal punch heads 323, 322, are not latched together. The disengagement of the distal punch head 322 and housing 310, and disengagement of the proximal and distal punch heads 323, 322, is caused by actuation of the trigger 311, as further discussed below. As described in the method illustration of FIGS. 6A-6G, below, this configuration would arise after a bone hole is created, and is used to introduce an anchor/suture into the anchor delivery tube for implant. To facilitate such a step in the procedure, a portion of the anchor delivery tube 330 referred to as the nub 332 remains extended from the distal end of the elongate tube 306, as shown by FIG. 3F. With the bone punch retracted or removed, the anchor delivery tube 330 now defines an open lumen 333 to allow an anchor to be introduced and passed therethrough with the aid of the re-inserted bone punch, as detailed below. As also highlighted in FIG. 3F, optionally, the distal end of the elongate tube 306 may be tapered as shown at 308. The taper 308, in some examples, provides the elongate tube 306 with a blunt distal tip that can be used to maintain force against the outside of a tendon during manipulation of an anchor and/or tensioning of a stitch between two anchors.

At a high level, the procedure may be understood as follows. With the anchor delivery device 300 in the configuration shown in FIGS. 3A/3D, the physician may probe the surgical site to identify a location where an anchor is to be implanted. Once the desired location is identified, the physician applies force to the tapping surface 324 of the bone punch to force the bone punch through the tendon and to create a bone hole using the distal tip 321 of the punch pin 320. As the physician advances the bone punch in this manner, the proximal and distal punch heads 323, 322 will become latched together to form the configuration as shown in FIGS. 3B/3E. The same action of advancing the bone punch relative to the elongate tube also advances the anchor delivery tube 330 and nub 332 beyond the distal end of the elongate tube 306. Next, the trigger 311 is actuated to release the bone punch, pushing the bone punch in a proximal direction to create the configuration as shown in FIGS. 3C/3F. The implant tool 300 is held in position, using the nub 332 to maintain registration with the formed bone hole. In some examples, a portion of the nub will be inserted into the bone hole. An anchor is then introduced into the anchor delivery tube 330 and passed down the lumen 333 thereof to the distal end, with force applied to advance the anchor using the bone punch assembly. Complete insertion of the anchor can be confirmed by maintaining pressure against the tendon to hold the nub 332 in the desired registration relative to the bone hole, and pushing the proximal punch head 323 in the distal direction until the distal punch head 322 latches with the proximal housing 310 and the proximal punch head 323 latches with the distal punch head 322. Now the trigger 311 will again be actuated, however, due to mechanisms that will be explained below, this second actuation of the trigger after insertion of the anchor will apply positive retraction force, along with spring force, to retract the anchor delivery tube 330 and nub 332 into the distal end of the elongate tube 306, as well as retracting the bone punch. With the nub retracted, the physician can manipulate toggling of the anchor using the working suture without the nub 332 possibly damaging the working suture, while force can be maintained against the tendon and bone by pressing the distal tip of the elongated tube 306 against the tendon. After toggling the anchor, the delivery tool 300 is pulled back from the implant position and the suture lock is secured by pulling on the suture lock cord. If the anchor is the second or a subsequent anchor in a series, the physician may tighten the working suture to form a stitch while keeping pressure against the tendon with the elongated tube 306 prior to moving the delivery device to a next position. The delivery device is then reset and the configuration of FIG. 3A/3D is again assumed.

Figure 3G:
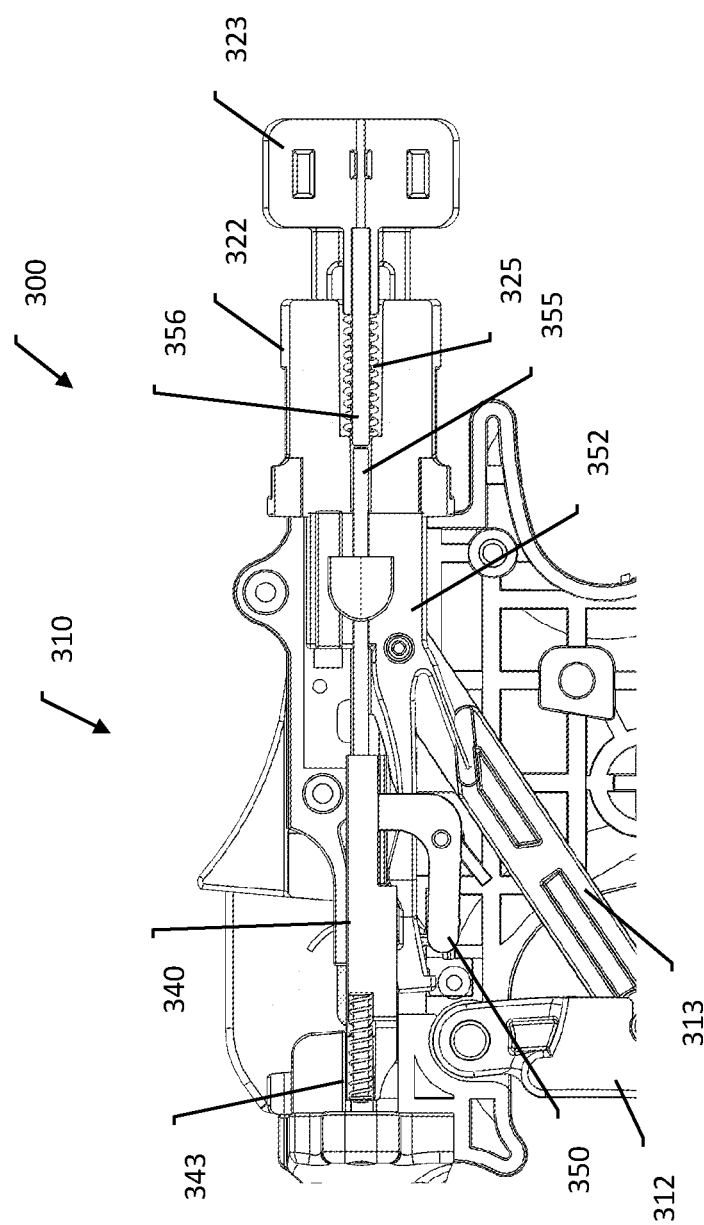
FIGS. 3G-3I are partial cut-away views of the anchor delivery device in several configurations.
Figure 3H:
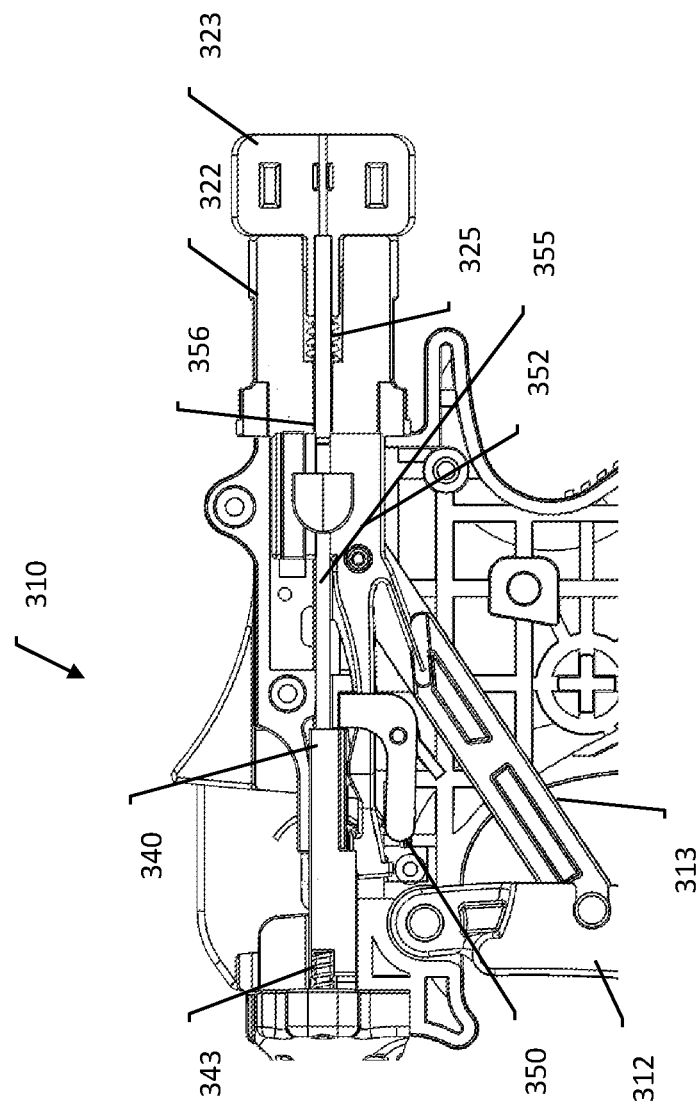
Figure 3I:
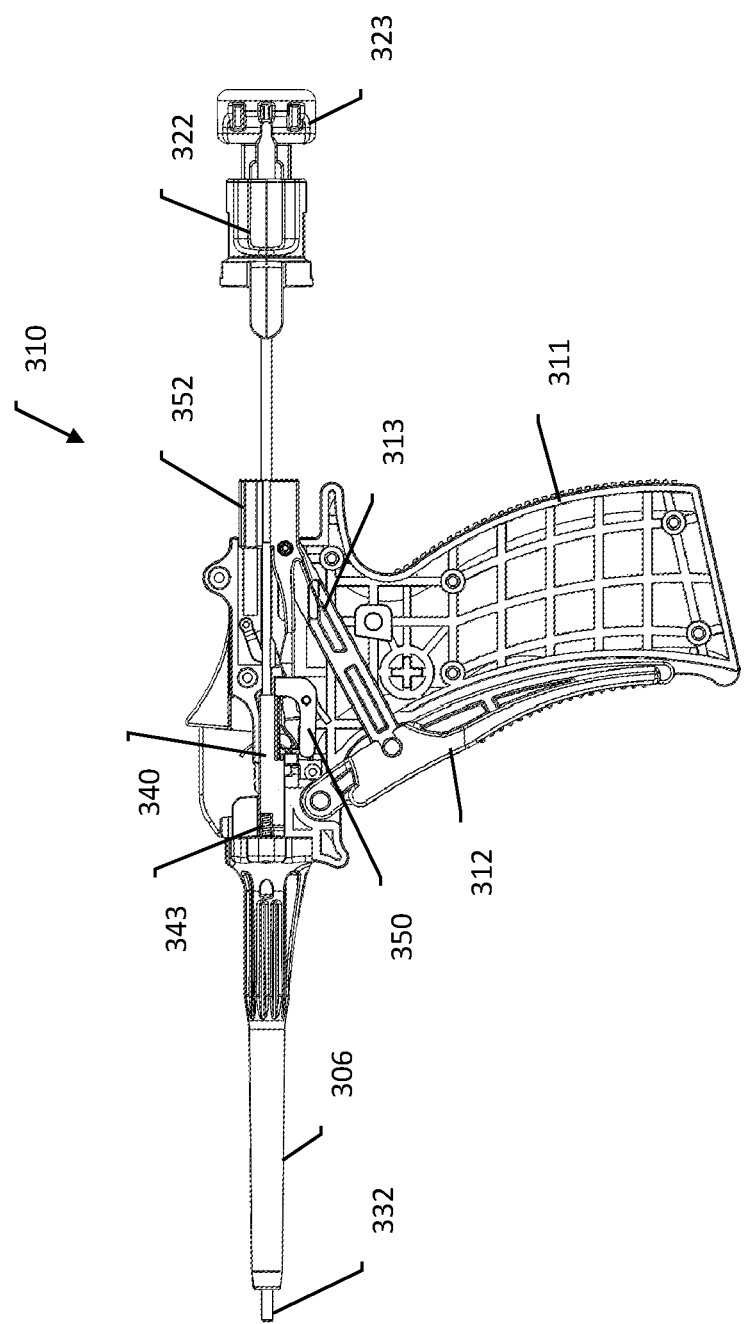

Turning now to the detailed mechanics of an illustrative example shown in the drawings, FIGS. 3G-3I are partial cut-away views of the anchor delivery device in several configurations. FIG. 3G generally corresponds to the configuration of FIGS. 3A/3D, in which the distal punch head 322 is latched to the proximal housing 310, and the proximal punch head 323 is not latched against the distal punch head, as can be confirmed in the drawing by noting that punch head spring 325 is in an extended position. A nub coupler bar 355 is illustrated, and is pushed forward by the proximal punch head via proximal punch head pin 356, having a ridge thereon to interact with the nub coupler bar 355. The device contains a slide stop 350 and an ejector 352. The ejector 352 is in turn secured to a trigger coupler 313 that is pivotably attached at one end to the trigger 312 and at its other end to the ejector 352. The ejector 352, at its own proximal end in the configuration shown, rests against the distal punch head 322. The anchor delivery tube is connected at its proximal end to a nub sub coupler 340 which is itself spring loaded by nub spring 343 relative to the proximal housing 310. As noted with respect to FIG. 3D, in this configuration the anchor delivery tube nub is retracted into the elongate tube, meaning that the nub spring 343 is in a relaxed state, as shown.

FIG. 3H corresponds to the configuration of FIGS. 3B/3E, in which the distal punch head 322 is latched to the proximal housing 310, and the proximal punch head 323 is now latched to the distal punch head 322, as can be confirmed in the drawing by noting that punch head spring 325 is now compressed. The same action of pushing the proximal punch head 323 to latch with the distal punch head 322 also pushes the nub coupler bar 355 distally, in turn pushing the nub sub coupler 340 and anchor delivery tube in a distal direction, compressing the nub spring 343 and advancing the anchor delivery tube so that the nub extends from the distal end of the elongate shaft, as shown by FIG. 3E. This movement also changes the juxtaposition of the slide stop 350 and the nub sub coupler 340, which, as can be seen, are now positioned so that the proximal edge of the nub sub coupler 340 is distal of an upper portion of the slide stop 350.

FIG. 3I shows the use of the trigger 312 to force a change of configuration from that of FIGS. 3B/3E to that of FIGS. 3C/3F. Here, the trigger 312 is squeezed against the grip 311. The trigger coupler 313 forces the ejector 352 to move proximally, overcoming the latch force of the proximal and distal punch heads 323, 322 relative to the housing 310 and disengaging a latch coupling the proximal and distal punch heads 323, 322 to each other (see FIG. 3R, below), forcing retraction of the bone punch. However, the nub 332 is not retracted into the elongate tube 306 because the slide stop 350 engages with the nub sub coupler 340, blocking it from moving in the proximal direction. The nub spring 343 stays compressed.

Figure 3J:
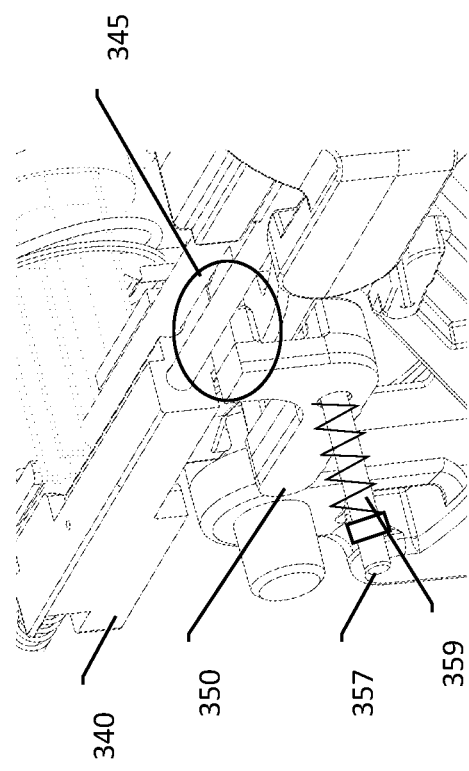
Figure 3K:
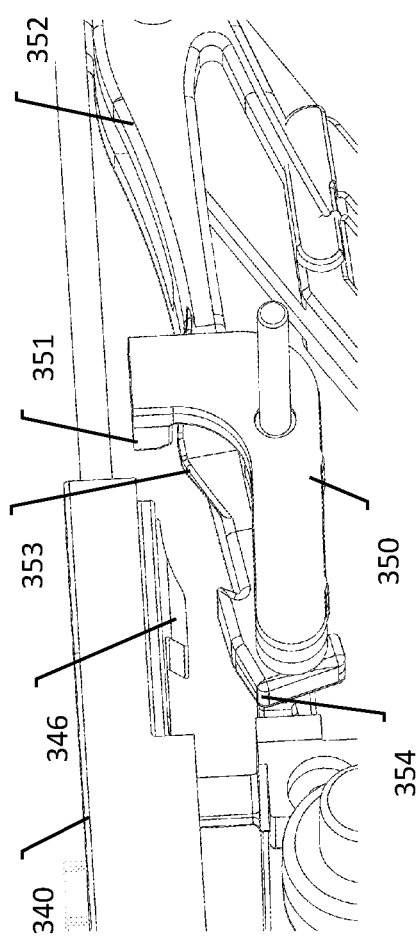

FIG. 3J shows in a closer view, taken from a rear angle as a partial cut-away view of the proximal housing. Here it can be seen that the nub sub coupler 340 abuts against the slide stop 350 at location 345. The slide stop 350 is carried on a pin 357, to allow lateral movement as will be further noted below. The pin 357 carries a slide stop spring 359 that pushes the slide stop 350 laterally toward the position shown in FIG. 3J. An additional function of the slide stop 350 is illustrated in FIG. 3K, which provides another angle to view the partial cut-away (with the slide stop spring 359 omitted). Here, the slide stop 350 includes an extension at 351 which is the part that will abut against the nub sub coupler 340 in the step shown in FIG. 3I/3J. Also visible is a ramp 353 on the ejector 352 which will push against the extension 351 to prevent an ejector hook 354 from engaging with a corresponding nub sub coupler hook 346 by pressing the ejector 352 down. As can be seen, the slide stop 350 in this configuration prevents retraction of the nub by limiting the movement of the nub sub coupler 340 in the proximal direction and also preventing engagement of the ejector hook 354 with the nub sub coupler hook 346.

Figure 3L:
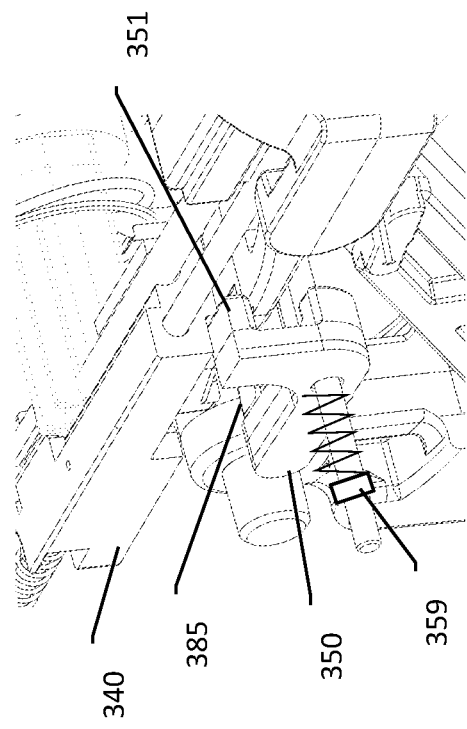
Figure 3M:
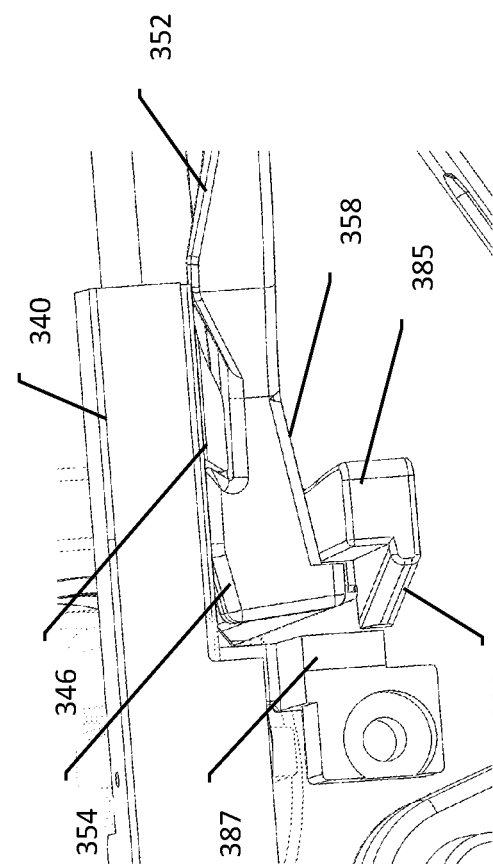
Figure 30:
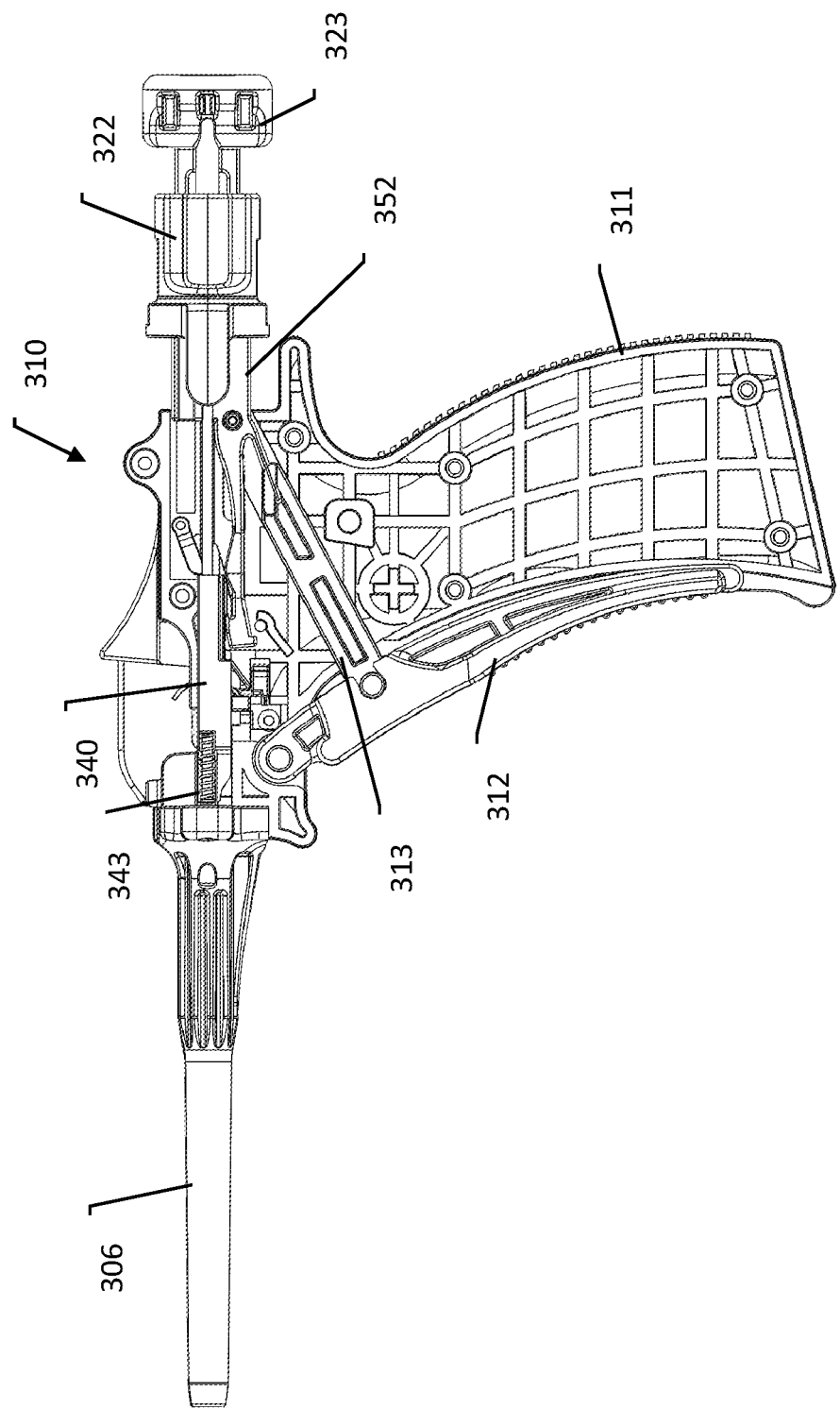

FIGS. 3L-3N are partial cut-away views further illustrating the interaction of internal components of the anchor delivery device. FIG. 3L illustrates decoupling of the slide stop 350 from the nub sub coupler 340 and the ejector 352. A plunger control arm 385, which is inserted as shown below in FIGS. 4A-4D, pushes the slide stop laterally so that the nub sub coupler 340 cannot engage with the extension 351, and also moves the slide stop along the pin 357 so that the ejector 352 no longer presses against the extension 351 when moved in a proximal direction. The slide stop spring 359 is thus compressed, and remains so until the nub sub coupler 340 is again advanced when pounded to create the next bone hole. In an alternative arrangement, decoupling of the slide stop 350 from the nub sub coupler 340 may be achieved by having item 385 coupled to a switch or lever on the housing, rather than using the plunger action, if desired. The position of the slide stop spring 359 is illustrative; other configurations and positions may be used.

The movement of the slide stop 350 allows a different interaction to occur when the trigger is subsequently pulled, as highlighted in FIG. 3M. Now, when the trigger is squeezed, the slide stop is no longer blocking movement of other parts, and so the slide stop is omitted from the view of FIG. 3M. The assembly remains extended until trigger actuation even with the slide stop moved laterally due to the latching of the proximal and distal punch heads to one another and latching of the distal punch head to the proximal housing. Here, it can be seen that the proximal end of the nub sub coupler 340 is free to move proximally. Moreover, positive retraction force can be applied by the ejector 352 when it is forced in the proximal direction by the trigger, because the ejector hook 354 can now engage with the corresponding nub sub coupler hook 346. To ensure the hooks 346 and 354 interact, a ramp 358 on the underside of the ejector 352 presses against the plunger control arm 385. The resulting action is shown by the view in FIG. 3N, which shows how the nub sub coupler 340 moves past the slide stop 350, allowing retraction of the nub when desired, using force applied via the trigger actuation as well as force applied by the nub spring 343.

FIG. 3O is a partial cut-away view of the anchor delivery device during a second actuation of the trigger. Here, the trigger 312 is squeezed against the grip 311, and the trigger bar 313 forces the ejector 352 in a proximal direction, unlatching the distal punch head 322 from the proximal housing 310. With the slide stop moved laterally out of the way, the nub sub coupler 340 is forced in a proximal direction as well, under the positive force applied by the trigger 311 via trigger bar 313, ejector 352, and hooks 354, 346 (FIG. 3M). By positive force, what is meant is that more than the spring force is being applied, such as by the mechanical linkage of the trigger 311, trigger bar 313, ejector 352 and hooks 354, 346. In addition, the nub spring 343 also provides force to move the nub proximally and will hold the nub in the retracted position inside the elongate tube 306 until the nub is used again for placement of another anchor.

Figure 3P:
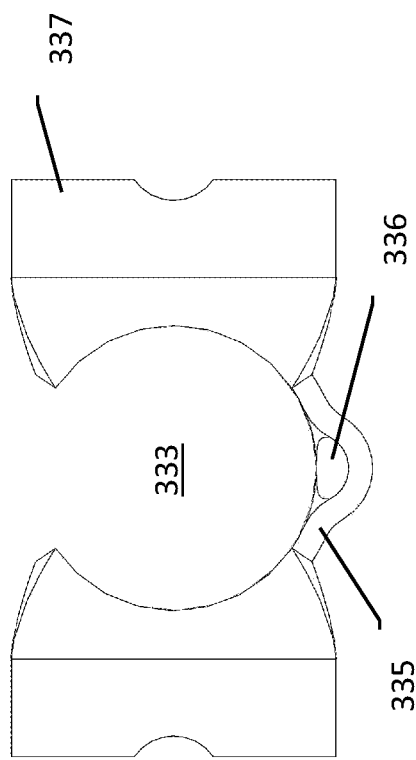
FIGS. 3P and 3Q display features of an illustrative anchor delivery tube.
Figure 3Q:
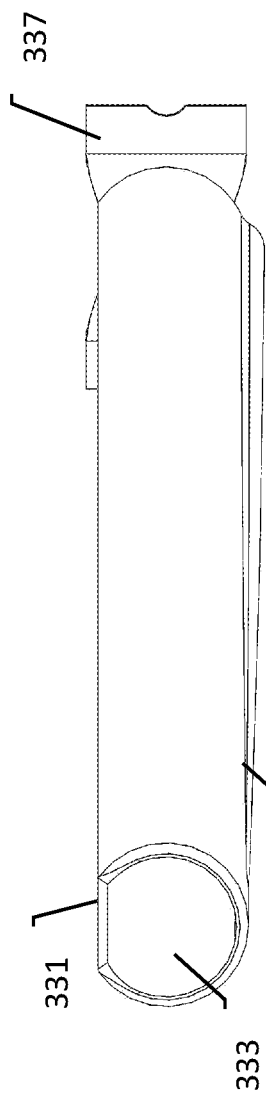

FIGS. 3P and 3Q depict features of an illustrative anchor delivery tube. The anchor delivery tube 330, in this example, has a slot at 331 through which sutures as well as the suture lock cord can pass during use. An inner lumen is defined as shown at 333, through which anchors can pass, as well as the bone punch. If desired, the lower surface of the anchor delivery tube 330 may be stamped or otherwise formed with an indentation or internal trough or channel, as shown at 335, to accommodate a suture 336 passing on the lower side of the anchor delivery tube 330. Such stamping may not be necessary in some examples, depending on the size of sutures used and how closely the features of the anchor and the anchor delivery tube lumen 333 line up. The proximal end of the anchor delivery tube may be formed with, or may have added thereto, additional material shown at 337 for securing within the proximal housing 310.

In an alternative configuration, the anchor delivery tube may be replaced by a push wire coupled to a relatively short nub portion having a slotted cylindrical shape. The nub portion may have a length of 3-5 centimeters, for example, such that a portion thereof can extend from within the lumen of the elongate tube 306 without entirely exiting the elongate tube. The push wire can then extend up the elongate tube to the proximal housing, where it would then be physically coupled to the nub sub coupler 340. Thus a full-length anchor delivery tube may be replaced with a shorter nub portion, if desired. The push wire (as well as the anchor delivery tube) may be pushed in the distal direction when the bone punch is advanced at the proximal end thereof (by including a pusher or linkage attached to the push wire or the nub sub coupler for example) if desired, or at the distal end thereof (by providing a shoulder for example toward the distal end of the bone punch to interact with the nub and/or a short anchor delivery tube).

Figure 3R:
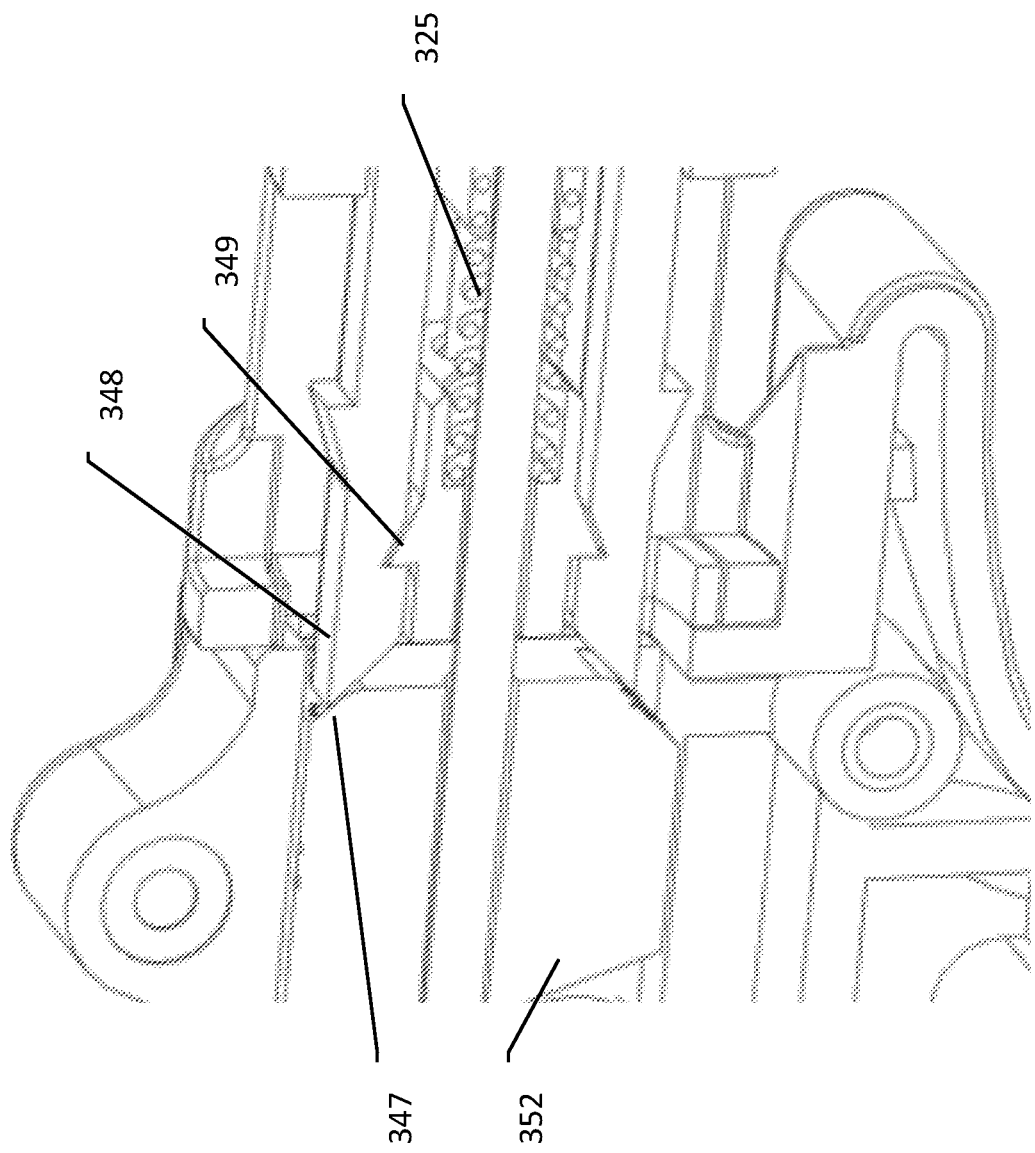
FIG. 3R illustrates coupling of the punch head.

FIG. 3R illustrates coupling of the bone punch assembly. In FIG. 3R, the ejector 352 is shown, including its proximal end having an angled surface at 347. The angled surface at 347 is aligned with latch arm 348, which is itself part of the proximal punch head. The latch arm 348 is shown engaged with spring base 349, which is part of the distal punch head, and carries the punch head spring 325. As can then be understood, as the trigger is depressed, the ejector 352 will move in a proximal direction, engaging latch arm 348 and pushing the latch arm 348 outward, disengaging the latch arm 348 from the spring base 349, releasing the proximal punch head from the distal punch head. In some examples, the physician may use this maneuver without causing the distal punch head to disengage from the housing, such as by lightly pulling the trigger, causing the proximal punch head to release from the distal punch head and thereby retracting the punch pin and pointed distal tip. As a result, this feature allows the physician to readily control how far the distal tip of the punch pin extends beyond the nub and/or the distal end of the outer tube of the anchor delivery device.

FIGS. 4A-4D illustrate features of a plunger for delivering anchors from individual cartridges to the delivery device and a magazine for holding cartridges on the anchor delivery device. Starting with FIG. 4A, the delivery device is generally shown at 300 with the proximal housing at 310. On one side of the proximal housing is a receiver 370 into which a plunger 380 can be slidably placed and retained. The top of the receiver includes a slot 372 for receiving a cartridge 392 that carries an anchor to be implanted. The cartridge 392 can be seen to have at least first and second ends of a working suture 393 extending therefrom.

The delivery device is shown relative to a patient 400 having a patient portal 402, which may be for example a shoulder portal that is formed for performing arthroscopic surgery. In the example shown, the removed cartridge 392 is shown with the working suture 393 extending on either side thereof. The physician may pull the cartridge away from the magazine and the delivery device, as well as the portal 402, in order to floss the working suture 393 so that an amount of slack is available on either side of the anchor contained in the cartridge 392. The purpose of this maneuver is to ensure that as the anchor is advanced through the delivery device and into the patient, there will be enough slack to make this passage easy. That is, while it is possible to floss the suture through the anchor during delivery and implantation, it may be preferable to generate slack before the implantation to make advancement of the anchor into position relatively easier. Once the anchor is positioned, the extra slack can be taken out as the physician tensions the working suture to create a stitch between the anchor being toggled and a previously placed anchor.

Opposite the plunger 380 is a magazine 390 that can be releasably secured to the proximal housing 310 and carries a plurality of cartridges 391. A cartridge ejector is shown at 394 for ejecting cartridges 391/392 one at a time. The magazine is shown with 7 cartridges 391 therein, the $8^{th}$ cartridge 392 having already been ejected. In the example shown, at least one additional cartridge has already been ejected and used, since the working suture 393 can be seen to extend into the elongate tube 306 and into the patient portal 402. It will be understood as well that the magazine is carried on receiver 398 (FIG. 3A). Greater detail regarding the magazine and its use can be found in U.S. patent application Ser. No. 17/551,811, filed Dec. 15, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference.

Figure 4C:
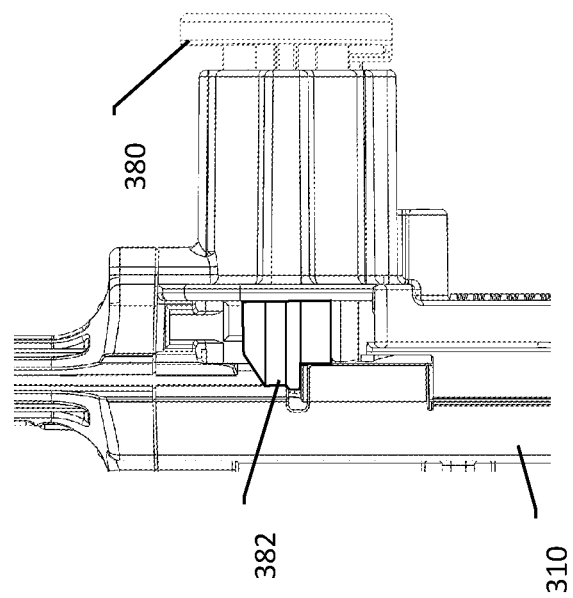
Figure 4B:
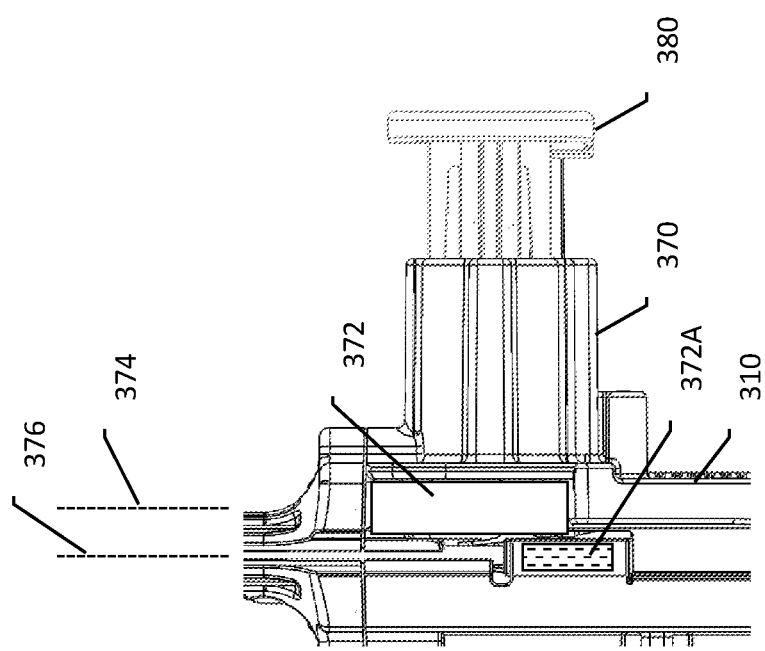

More details of the plunger and receiver are shown in FIGS. 4B and 4C. Starting with FIG. 4B, the plunger itself is shown at 380, in an extended position relative to a receiver 370. The slot 372 can be observed in this top view of the proximal housing 310. When a cartridge (not shown) is placed in the slot 372, the plunger can be depressed as shown in FIG. 4C. Doing so laterally transfers the anchor from the cartridge into the bore through the length of the delivery device. The anchor is then ready to be inserted by advancing the bone punch through the proximal housing and down the anchor delivery lumen. Referring back to FIG. 4B, the anchor is carried in a cartridge 392 such that when the cartridge 392 is inserted into slot 372, the anchor generally lies along line 374, while the midline of the anchor delivery tube is shown generally at 376. The plunger prepares the anchor for delivery by pushing the anchor laterally to the midline of the anchor delivery tube at 376, and holds the anchor in position until the bone punch is advanced to push the anchor down the anchor delivery tube.

In addition, the plunger being depressed causes the changes in configuration previously described within the proximal housing. In particular, in the illustrative example that is shown herein, depressing the plunger moves the slide stop 350 discussed above laterally out of the way of the nub sub coupler 340 and out of the way of the ejector 352, allowing the retraction of the nub after the anchor has been inserted. In some examples, the anchor delivery device will not allow the plunger to be actuated from its extended position to its depressed position while the bone punch is extended down the lumen of the anchor delivery tube. That is, until the bone punch has been retracted after a physician has first actuated the trigger, the plunger cannot be depressed fully in some examples.

Figure 4D:
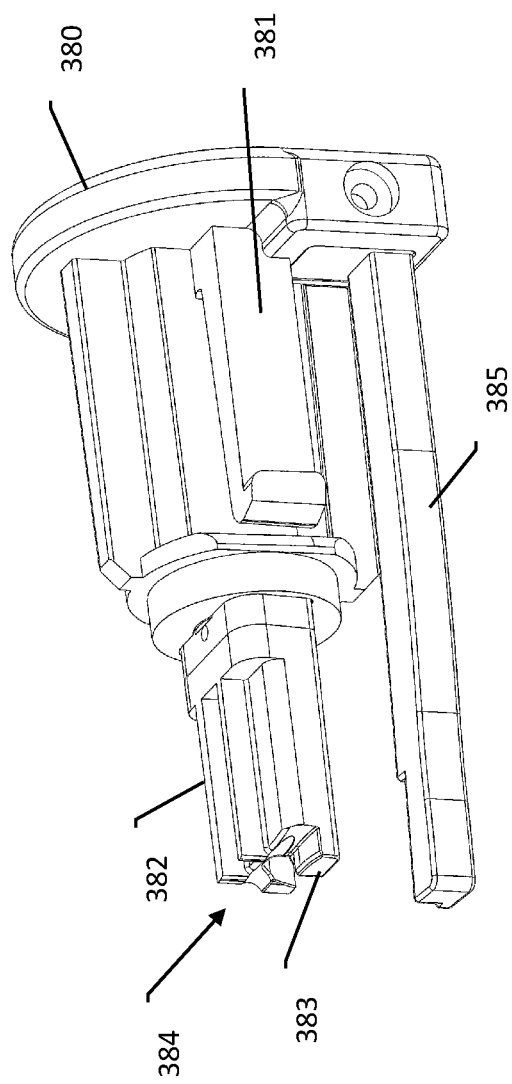

FIG. 4D shows the plunger in isolation. Here, the plunger 380 can be seen to include an anchor pusher 384 including an anchor platform 383 that sits under the anchor, and matching bars 382 that extend into matching slots of the cartridge. The plunger control arm 385 is also shown. The control arm 385 is the element discussed previously that moves the slide stop 350 laterally to allow retraction of the anchor delivery tube and nub after the anchor is fully implanted. The control arm 385 also serves to push the ejector 352 upwards when in position to ensure coupling of the ejector (and hence the trigger) to the nub sub coupler that in turn attaches to the anchor delivery tube and nub. Guide arms 381 are used to guide the plunger 380 as it slides in and out of the receiver 370.

Referring back to FIG. 3M, the plunger latch 386 (not visible in FIG. 4D) is carried on the control arm 385. The plunger latch 386, when the plunger is fully inserted, rests against plunger catch 387 to prevent removal of the plunger 380. When the ejector 352 is used to pull back the nub sub coupler 340, the bottom of the ejector 352 pushes the control arm 385 in a proximal direction and, as shown in FIG. 3M, allows the plunger latch 386 to be released once the nub and bone punch have been at least initially retracted. The body of the plunger 380 may connect to the anchor pusher 384, in some examples, with a wave spring (not shown, but residing inside the body of the plunger 380) that allows overtravel to ensure latching of the control arm 385 and plunger latch 386. When the plunger latch 386 is released, the wave spring (or another spring, if provided) pushes the plunger back to its extended position. The slide stop may also move back to its original position under spring pressure.

In an alternative configuration, the control arm 385 may not be part of the plunger, and may instead be coupled to a switch or lever on the proximal housing, allowing the physician to determine the mode of trigger operation without using a plunger. To this end, item 399 in FIG. 4A may be used as a switch or button to control position of the slide stop, for example.

Figure 5A:
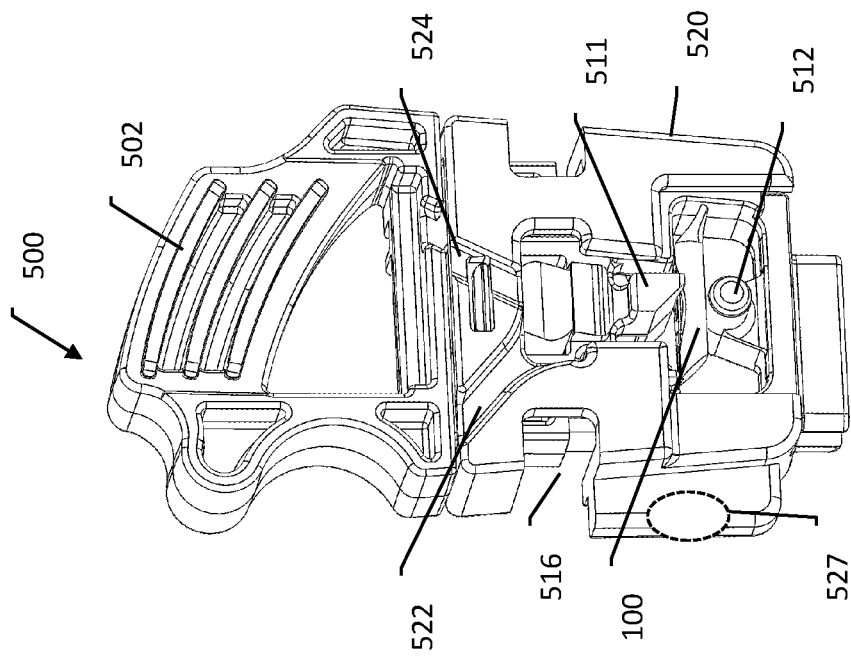
FIGS. 5A-5D illustrate a cartridge for holding a toggle anchor.

In another alternative, the slot 372 may be placed directly in line with the central axis 376 (FIG. 4B) of the anchor delivery tube, and rather than lateral movement out of the cartridge, an anchor may be placed in position for advancement down the anchor delivery tube directly. As an example, the slot 372 may instead be positioned at location 372A in FIG. 4B, and the plunger 380 and receiver 370 could then be omitted. For example, a physician may remove a pre-strung anchor from sterile packaging and directly place the anchor into a centrally positioned slot. Alternatively, a physician could place the anchor in a central slot such as that at 372A by insertion of the cartridge. While some examples herein show a cartridge configured for lateral removal of an anchor, in an alternative in which the cartridge is inserted in a centrally located slot (372A), a cartridge as shown in FIG. 5A/5B may instead have an opening as shown at 527 that allows removal of the anchor in an axial direction (such an arrangement may omit the boss 512 and/or has the working suture positioned on top of the boss 512 to allow axial movement). Other alternatives can be used as well.

To recap regarding the implantation procedure, the physician uses the configuration of FIG. 3A to probe the surgical site and identifies a location at which an anchor is to be placed. The physician then taps or pounds on the proximal punch head which causes the bone punch to advance. As the bone punch is advanced, the proximal punch head latches with the distal punch head, assuming the configuration of FIG. 3B, also forcing the nub distal of the distal end of the outer elongate tube. As the tapping force is applied, each of the bone punch pin and tip extend through the tendon and into bone, and the nub is pushed into registration with the bone hole, at least partly engaging the nub with the bone hole. While this order of operations is useful in one example, the steps may be reordered as desired, such as by latching the punch head together prior to probing, if desired.

The physician then pulls the trigger a first time. Because the plunger is not engaged/depressed at this time, the trigger actuation results in retraction of the bone punch, but not the nub at the end of the anchor delivery tube. A cartridge is taken from the magazine, extended out from the magazine to create slack on either side of the cartridge in the working suture, and inserted into the slot for receiving cartridges on the delivery device housing. Before or after cartridge placement, the bone punch is retracted to a position that places the distal tip of the bone punch proximal of the location of the plunger, allowing the plunger to now be depressed. With the cartridge in place and bone punch retracted, the plunger is used to push the anchor into alignment with the anchor delivery tube. The bone punch is then advanced to push the anchor to and out of the distal tip of the anchor delivery tube. Full extension of the bone punch is demonstrated by latching the proximal punch head to the distal punch head, which is itself latched to the proximal housing of the delivery tool.

The physician will again squeeze the trigger. This second actuation of the trigger occurs with the plunger fully inserted, meaning that actuation of the trigger retracts the bone punch as well as the anchor delivery tube, as the plunger insertion will have moved the slide stop out of the path of the nub sub coupler and forces engagement of the ejector thereto, actively pulling the nub as well as the bone punch out of the bone hole. The same trigger action also releases the plunger as the ejector pushes the control bar to release the plunger under spring action. What remains, as discussed in FIGS. 6A-6I, are the steps of completing the toggling of the anchor and tensioning the working suture, followed by securing the suture lock, before moving on to the next anchor. Though not shown, the anchor delivery tool may optionally include a punch stop to prevent the bone punch from being removed entirely from the device.

FIGS. 5A-5D illustrate a cartridge for holding a toggle anchor. Starting with FIG. 5A, a cartridge 500 is illustrated with a handle 502 adapted for grasping by the user/physician. An inner holder is shown at 510, and is surrounded by a cover 520. The inner holder 510 secures an anchor 100 between an upper anchor support 511 and a boss 512. In the configuration shown in FIG. 5A, the cartridge is "closed" in that the anchor 100 cannot be removed.

Figure 5B:
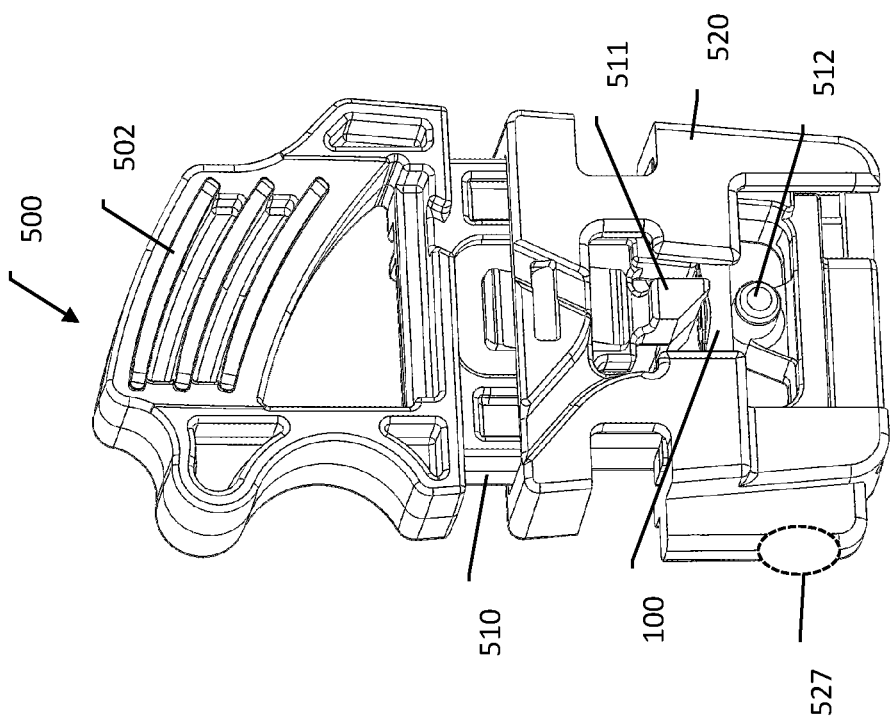

FIG. 5B shows the cover 520 raised to an "open" position in which the anchor 100 is no longer secured by the cover 520. The cover defines two channels at 522, 524. First channel 522 provides a path for the working suture out of the cartridge 500, and second channel 524 provides a path for the suture lock, as will be further detailed below. The cover may be spring biased to the closed position, if desired, to prevent inadvertent removal of the anchor 100 during handling. Alternatively, the cover can include detents to hold the cover in a closed position until pressure is applied during insertion. In addition, the upper anchor support 511 and boss 512 are spaced so that the anchor 100 is held in position against falling out.

As noted previously, an alternative design may have the inner holder 510 open in alignment with slot 527 to allow anchor removal in an axial, rather than lateral direction. For such an alternative, in an example, the upper anchor support 511 and boss 512 would be positioned higher up on the inner holder, such that the anchor 100 would be held at position 516 as shown in FIG. 5B.

Figures 5C, 5D:
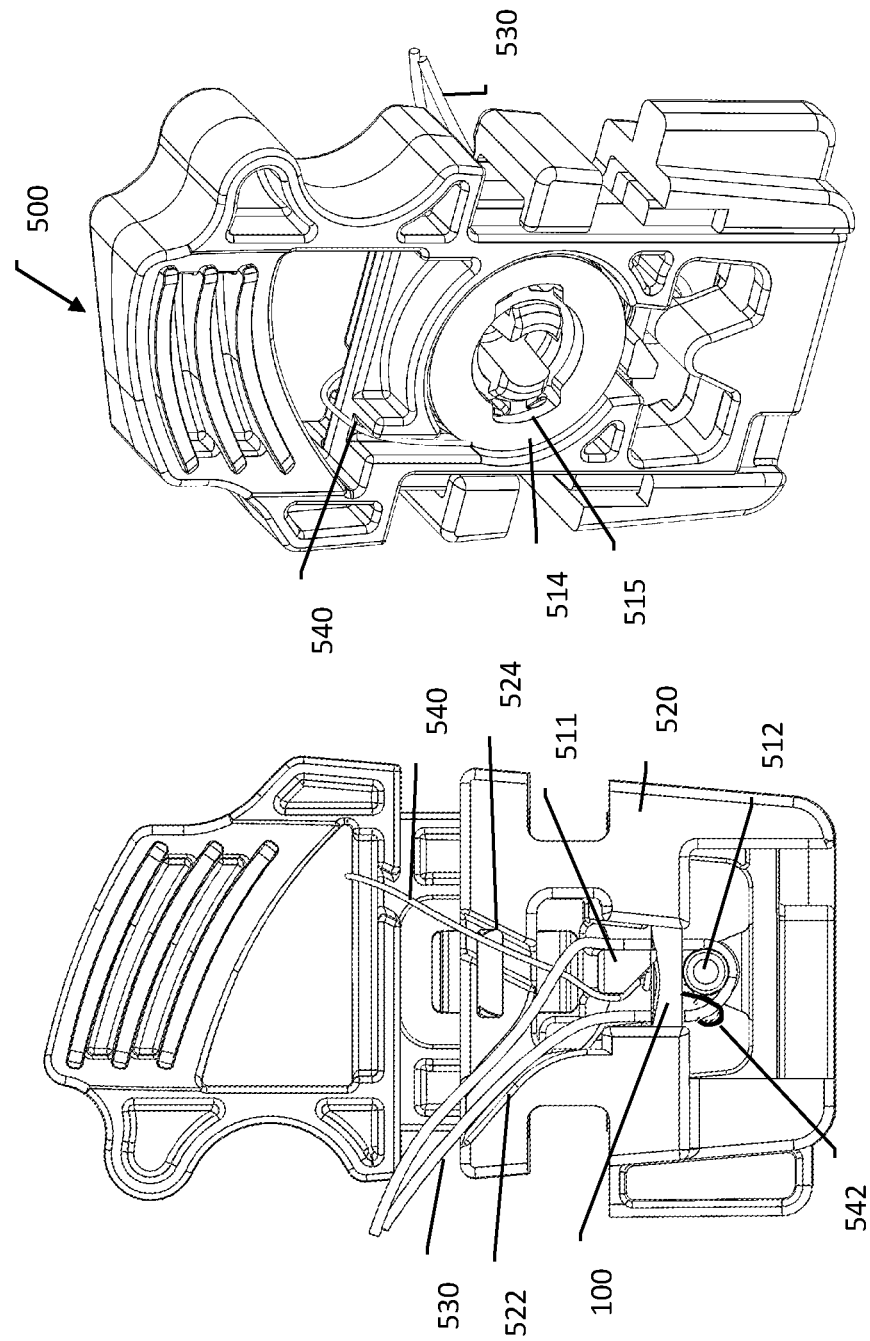

FIG. 5C shows the cartridge 500 in the closed position again with the cover down. The working suture 530 is now shown passing through first channel 522. The suture lock is shown as well, with the free end 540 of the suture lock passing through second channel 524 and the locking loop shown at 542. As can be seen, the boss 512 holds the working suture 530 away from the underside of the anchor 510, making flossing of the working suture easier prior to release of the anchor 510 from the cartridge. That is, because the bottom side of the anchor 510 may include a channel that makes flossing of the working suture therethrough more difficult, keeping the working suture 530 away from the bottom side of the anchor 100 may make flossing easier. Also, when the working suture 530 is pulled close to the bottom side of the anchor 100, the path that must be navigated when flossing includes first and second near ninety degree turns, increasing friction as the working suture 530 is flossed. Therefore, the boss 512 can be seen to make flossing easier in some examples. In other examples, the boss 512 may be designed so that the working suture does not wrap around it, and instead a simple support on the bottom side of the anchor 100 may be provided, with the working suture then resting between the support and the bottom side of the anchor. It may also be noted that having the working suture placed as shown may aid in retaining the anchor in place until it is ejected by the insertion of the plunger in the examples shown above.

FIG. 5D shows the back side of the cartridge 500. Of note here, the free end 540 of the locking loop 542 passes into a channel and then to a spool 514. In an example, the free end 540 is attached to the spool 514, such as by a knot, so that the free end can be pulled a select distance (10 to 20 cm, for example) before reaching a point where it can no longer unspool. When the physician seeks to use the locking loop, the cartridge 500 can be grasped and pulled until the spool runs out. The physician can then pull on the cartridge and therefore on the free end of the locking loop until the locking loop breaks at the break knot (or other preferential point of failure), as described below and above. The result is that the physician can manually grasp the cartridge to easily lock the locking loop and break the free end of the locking loop without needing a special tool and/or without needing to attempt to grasp the thin cord of the free end of the locking loop. It can be observed that the spool 514 includes inner features 515 allowing a tool to be inserted and twisted to spool the free end 540 of the locking loop onto the spool 514. As with the steps of toggling and/or tensioning a stitch, the distal end of the anchor delivery tool may be used to apply exterior pressure on the tendon as the locking loop is tightened and the free end is broken off.

Figure 5E:
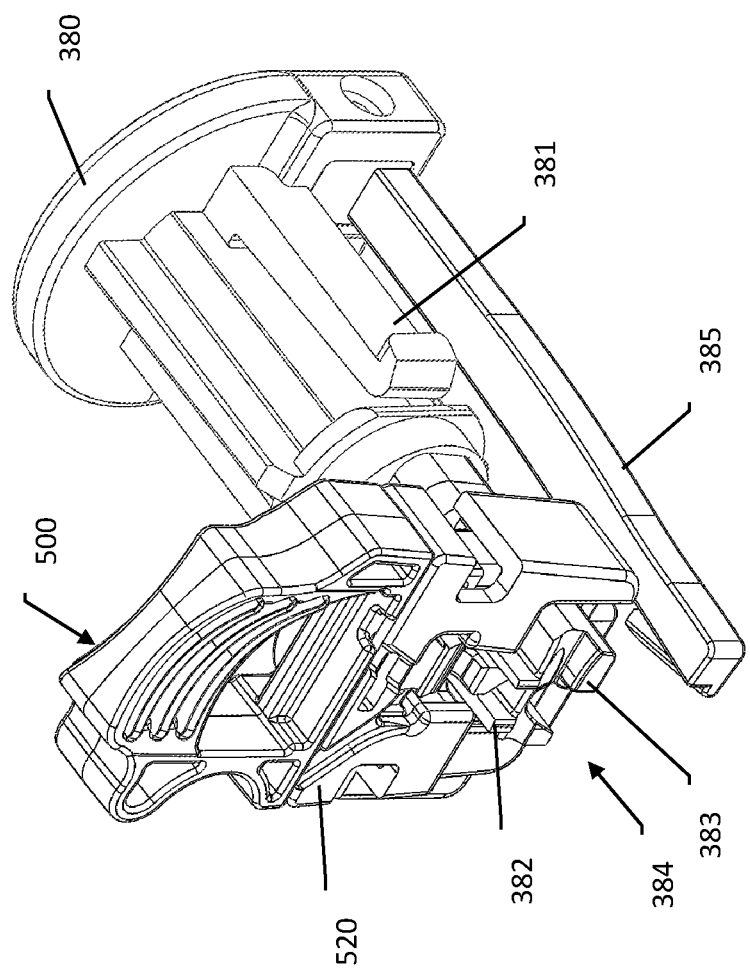
FIG. 5E illustrates interaction of a cartridge of FIGS. 5A-5D with a plunger as in FIGS. 4A-4D.

FIG. 5E illustrates interaction of a cartridge of FIGS. 5A-5D with a plunger as in FIGS. 4A-4D. The rest of the proximal housing of the anchor delivery tool is omitted, but it may be understood that insertion of the cartridge 500 into the slot for receiving the cartridge has now raised the cover 520 to an open position. The plunger is then slid into the position shown. With the plunger depressed, the anchor pusher structure 584 passes through the cartridge, with the anchor support 383 and matching rails 382 passing through the cartridge. The rails 382 pass on either side of the upper anchor supports 511, and ensure that the working suture is released from the cartridge when the plunger is depressed. As can also be seen, the control bar 385 is now inserted and performs the functions of moving the slide stop discussed above.

Additional details regarding an illustrative magazine and its use may be found in U.S. patent application Ser. No. 17/551,811, filed Dec. 15, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference.

It should be noted that the illustrative anchor implantation system shown is but one example of how the presently disclosed anchor system may be implanted. For example, a system that fully withdraws the distal end of the bone punch back to the proximal housing as shown may not be necessary. Separate cartridges for each bone anchor are illustrated in the implantation system; in other examples, several anchors may be disposed together in one cartridge in a longitudinal fashion, for example, for sequential loading. Another anchor delivery tool is disclosed, for example, in U.S. Provisional Patent Application Ser. No. 63/172,629, filed Apr. 8, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference. Rather than lateral release of an anchor from a cartridge, an axial release may be used. In some examples, a cartridge can be omitted entirely. Any suitable implantation system may be used, as desired.

In FIGS. 6A through 6G, an exemplary method for implanting individual and an array of anchors is depicted.

Figure 6A:
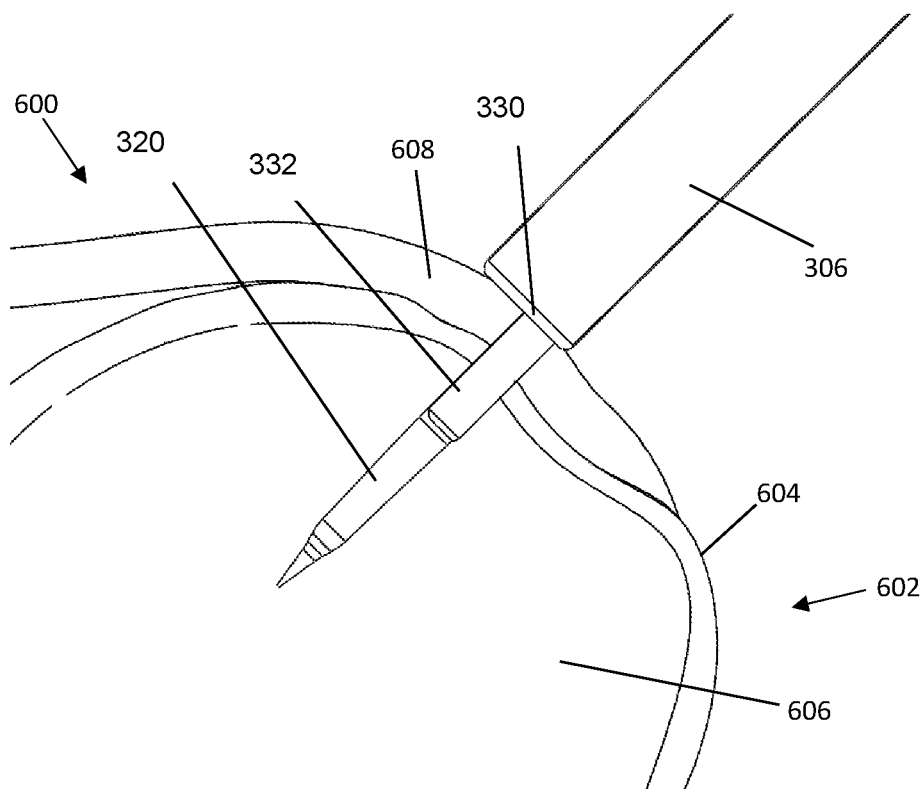
FIGS. 6A-6I illustrate the steps for implanting exemplary anchors of the current invention and resulting pattern of continuous tensioned and locked anchor to anchor single suture stitches.
Figure 6B:
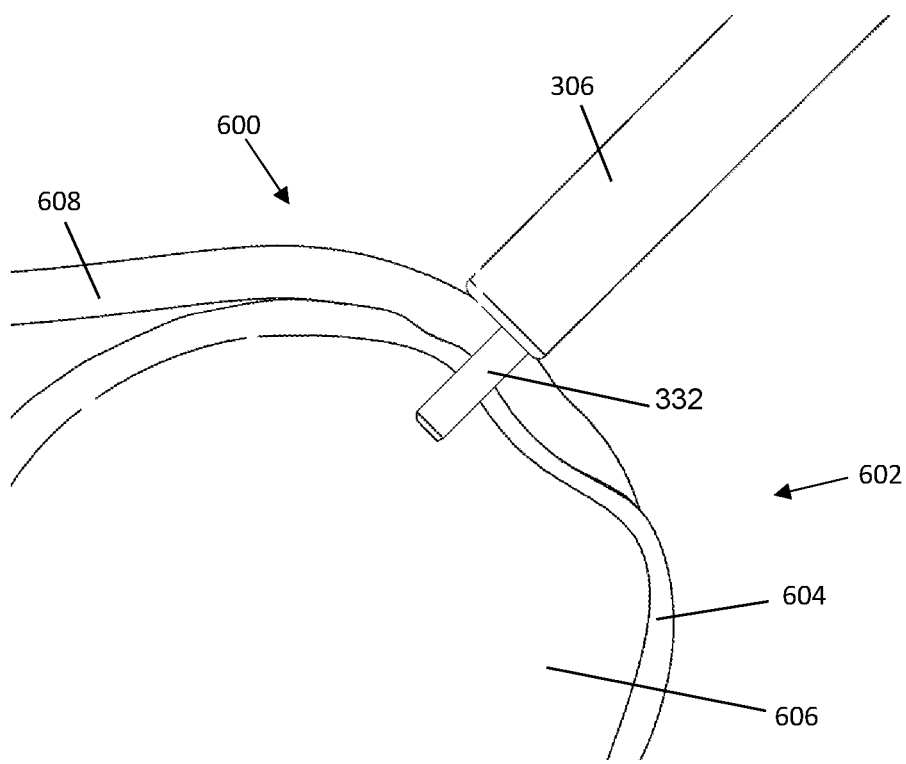
Figure 6C:
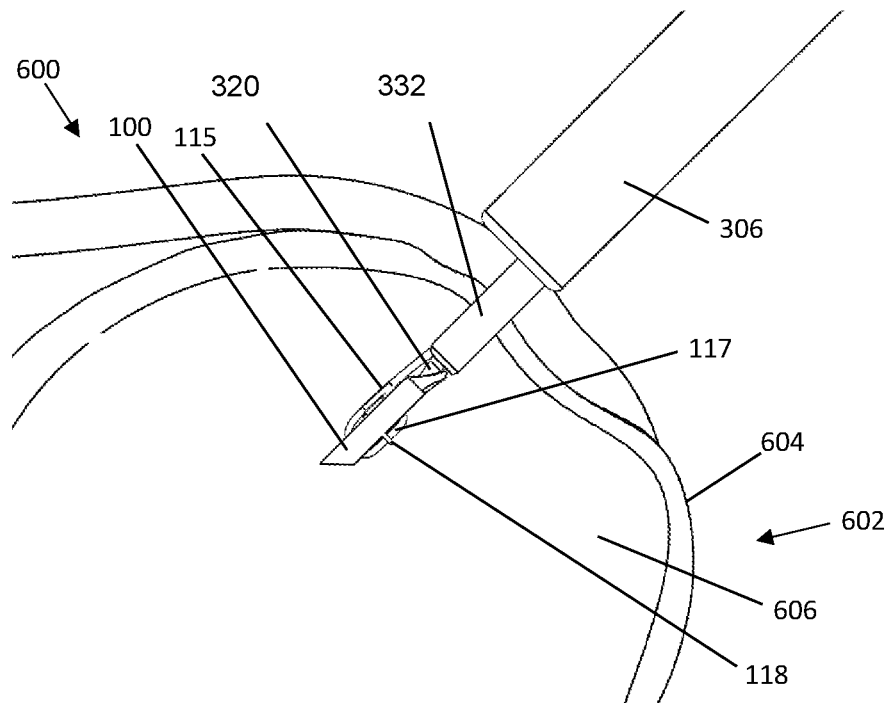
Figure 6D:
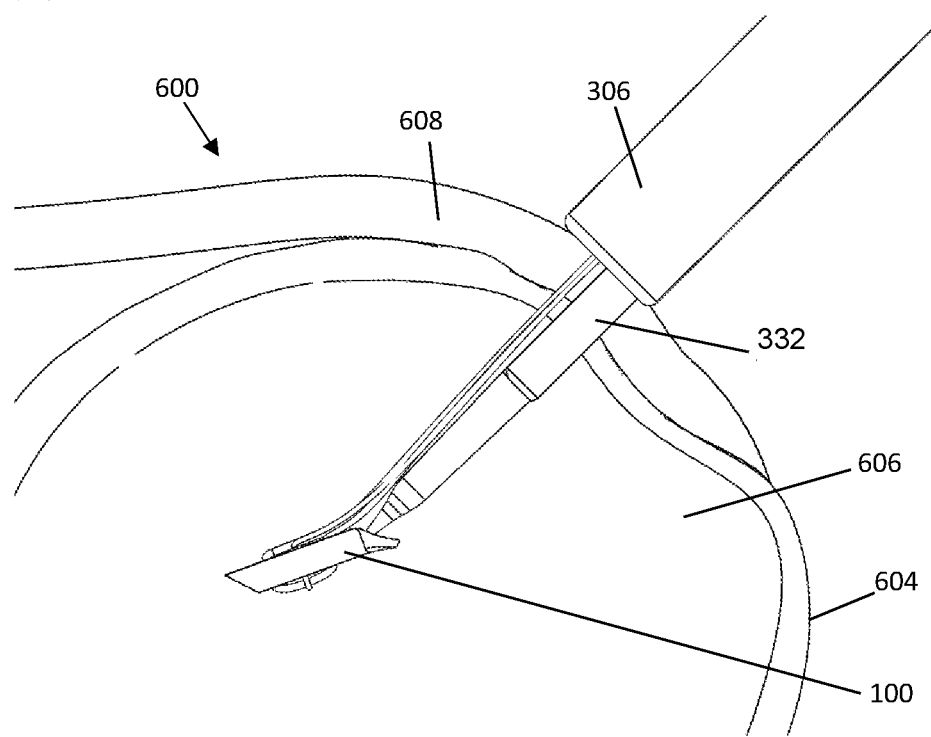
Figure 6E:
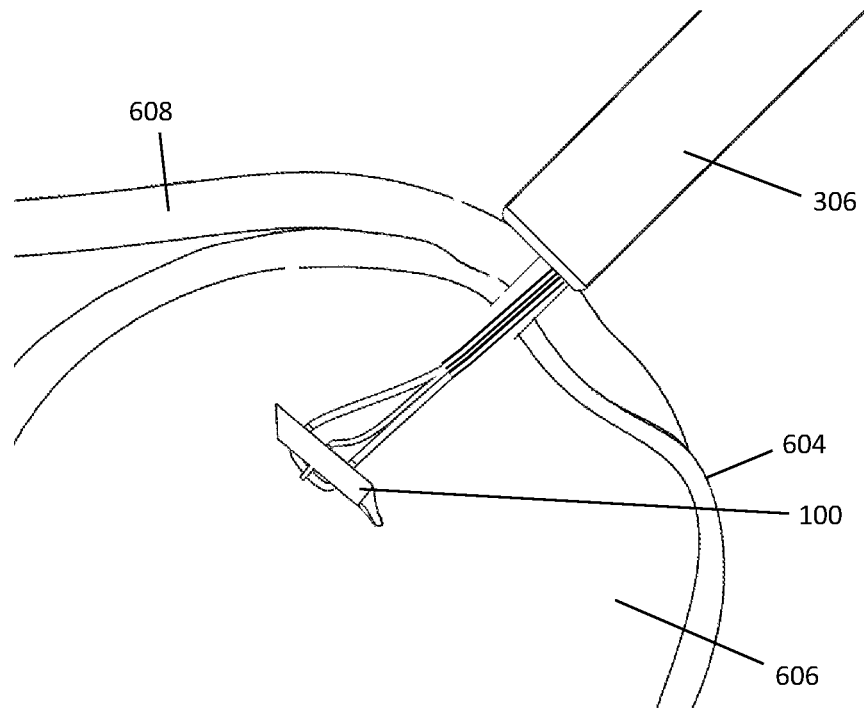
Figure 6F:
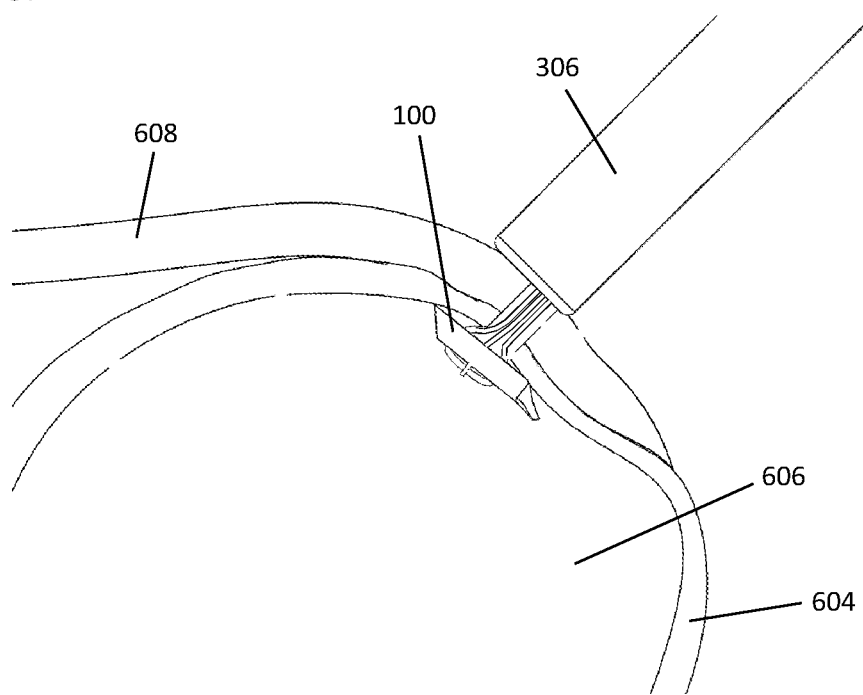
Figure 6G:
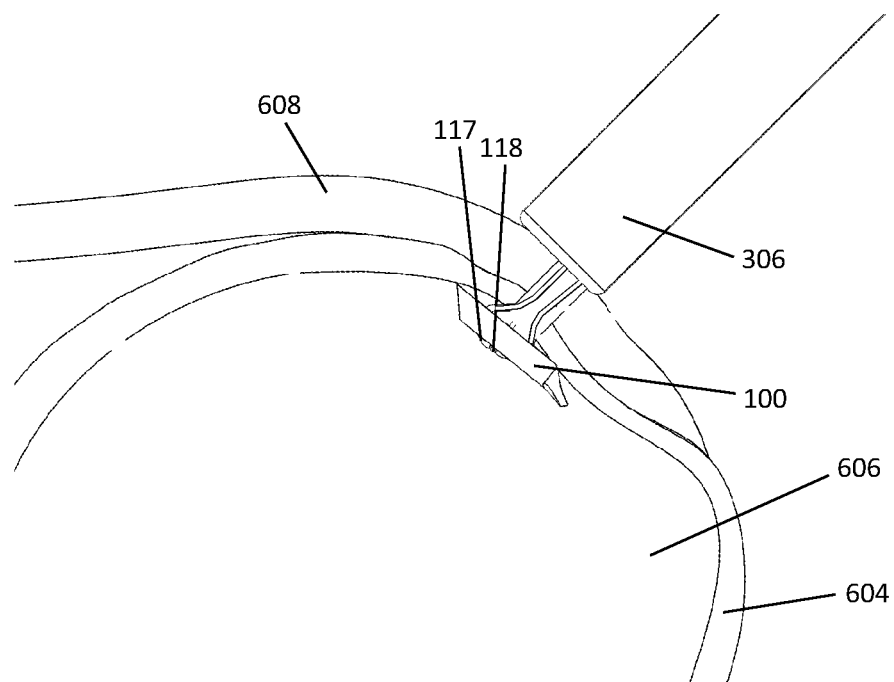
Figure 6H:
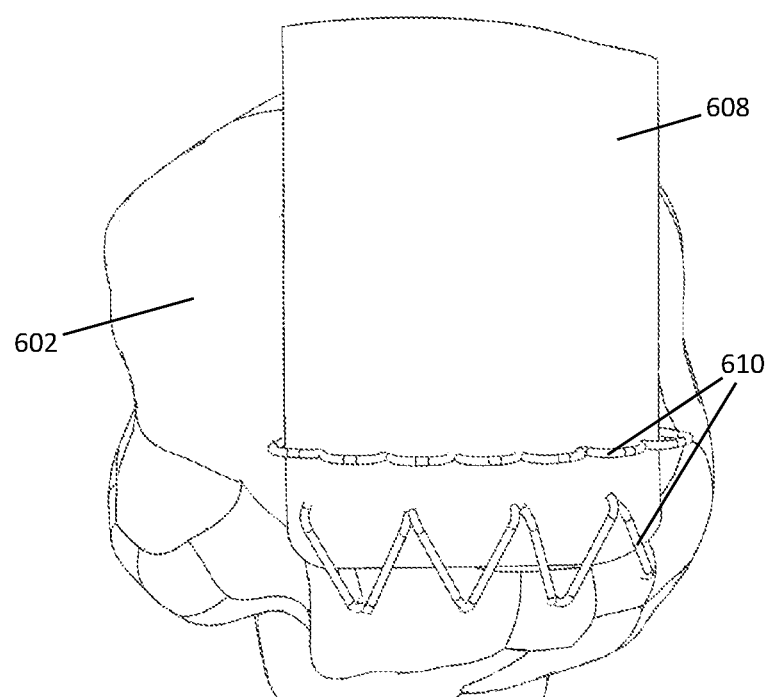
Figure 6I:
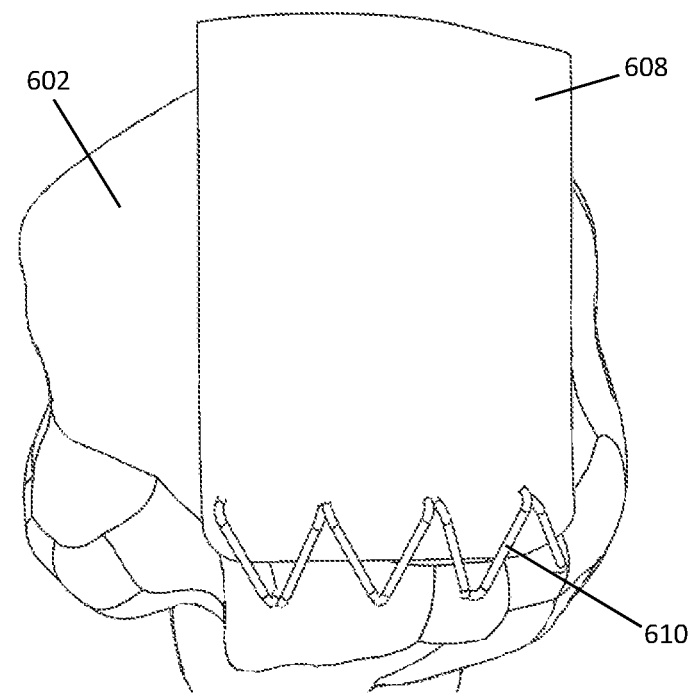

Further, FIGS. 6H and 6I illustrate example suture stitch arrays as implanted on the surface of a rotator cuff tendon having anchor to anchor continuous stitches that are independently tensioned and locked that can result from using this method.

Referring first to FIG. 6A, a schematic of select parts of the shoulder rotator cuff 600 is depicted in order to explain the methods of implantation. The illustration includes a portion of the humeral head 602 shown including an outer cortical shell layer 604 and an inner cancellous bone material 606. A tendon, in this case the supraspinatus tendon 608 is shown overlaying a portion of the humeral head where is attached to the footprint. The method is a transtendinous or through the tendon repair. The tendon 608 is first positioned in a desired location for reattachment to bone in the footprint of original attachment. The delivery device of FIGS. 3A-3R, or similar is then utilized to implant the toggle type suture anchor through the tendon 608. To begin the delivery device is set as in FIG. 3C with the distal nub 332 extending from the distal end of the implant delivery tube 330 and elongate tube 306. The bone punch 320 is fully inserted distally so that it extends beyond the distal end of the nub 332 and is locked in place, as is the nub locked in place. The device as configured is positioned on the tendon at the desired anchor placement and pounded in until the distal end of the outer tubular member is in contact with the tendon as shown in FIG. 6A. At this point the nub 332 extends through at least a portion of the cortical shell 604 (in thinner bone the nub 332 can extend into the cancellous bone 606) and the distal end of the bone punch 320 extends deeper into the cancellous bone 606. To achieve the desired depth of implantation to assure toggling, the bone punch extends beyond the elongate tube 306 distal end a distance of greater than or equal to about 20 mm. Further, to assure nub registration with the bone hole, the nub portion 332 extends beyond the elongate tube 306 distal end a distance of about 6 to about 10 mm.

As depicted in FIG. 6B, the bone punch 320 is then retracted while maintaining the elongate tube 306 and nub portion 332 in place, with the nub portion 332 providing registration with the formed hole in the bone. Absent such registration with the bone hole by the nub portion 332, the location under the tendon would be lost and it would be very difficult to feed an anchor through the tendon which would tend to fill the hole through which the bone punch traveled. In some examples, as described above, this step of the method may be performed by depressing a trigger on an implant tool where the implant tool is configured to maintain the nub portion 332 extended under certain circumstances (for example, with the slide stop in place) while applying a positive retraction force to the bone punch 320.

The first toggle type anchor is transferred or inserted into the proximal portion of the anchor delivery tube inside the elongate tube 306. As shown in FIG. 6C, the bone punch 320 is then reinserted into the lumen of the anchor delivery tube and advanced distally. As shown in FIG. 6C, the toggle body 100 of the anchor is pushed out the distal end by the bone punch 320. The bone punch 320 continues to be advanced in the distal direction to its original depth to push the toggle body 100 into the bone. It has been found that pushing the proximal end of the anchor deep into the bone with the toggle body 100 having an angled distal end causes or at least initiates rotation of the toggle body 100. This initial rotation assures continued rotation upon pulling tension on the working suture 115 outside the body.

As shown in FIG. 6E, the bone punch 320 and nub 332 are then retracted by the application of positive force by the trigger (as shown in examples above), as well as with spring action. This assures the nub 332 does not cut or fray the working suture. The bone hole remains shown in the drawings. The distal portion of the working suture extending from the distal passage is then pulled to complete the toggling of the anchor as aided by the proximal fins on the toggle body. This is shown in FIG. 6E. With continued tension on the working suture, the toggle body 100 is pulled toward the inside surface of the cortical shell of the bone as shown in FIG. 6F. To aid this step, the anchor delivery tool distal end may be pressed against the tendon to provide a counterforce against pullout during toggling and/or suture tensioning; that is, as the anchor is toggled and the suture is tensioned, the toggle body 100 may reach and press against the cortical shell. Additional counterforce can be applied in particular in regions of thinner cortical shell, such at the edges or outside of a tear footprint, and/or between the greater and lesser tubricals of the humerus. As depicted in FIG. 6G, once the working suture 115 is tensioned, the locking suture is tensioned to close the locking loop 118 around the working suture 115 and fix the working suture relative to the toggle body 100. In some examples, the locking suture is broken during this step at the knot which is at or inside the central bore of the anchor 100, thus, FIG. 6G shows only the working suture extending back into the elongate tube 306.

With implantation of the first anchor, the working suture 115 is simply locked as it cannot be tensioned to form a stitch until the second anchor is implant. In some examples, the first anchor in a chain of anchors can be pre-locked for this purpose; in other examples the surgeon will lock the first anchor suture lock at the time of implant. Therefore, in preferred methods, the second anchor is implanted repeating the above steps, except to the extent that the suture lock is differently engaged. As the working suture is pulled to toggle the anchor, any loose working suture between the first and second anchors is pulled through to form the tensioned stitch. During suture tensioning the distal end of the elongate tube 306 can be maintained against the outer surface of the tendon to prevent pullout or even possible bone fracture at the cortical shell. Once properly tensioned, the second anchor is locked. These steps are repeated for the rest of the anchors in an array.

As shown in FIGS. 6H and 6I, using the above method and device can create a row of continuous stitches that closely spaced, individually tensioned and tightened. A preferred pattern includes a row of stitches generally perpendicular to the direction of the tendon as shown in FIG. 6H. In a rotator cuff repair these would all be placed in a medial portion of the original tendon footprint. In some preferred embodiments a second row of anchors is also implanted, especially in a rotator cuff repair. The second row is implanted laterally of the first row and can include a zig zag pattern to put some anchors in the lateral portion of the original footprint and other anchors lateral of the footprint to hold down edges of the torn tendon. Other configurations are also possible depending on the size and shape of the tear. For example, on a small tear a single zig zag row of stitches could be used as shown in FIG. 6I. Anchors may also be placed to create stitches over attached portions of the tendon to reinforce the margins/edges of fully or partially torn tendons.

The preceding provides a relatively complete description of the anchor itself, pre-strung anchor arrays, suture lock, cartridge, magazine, and anchor delivery tool. A range of inventions are thus disclosed, and not all components or parts needs to be used together. For example, the delivery tool may be configured to for use with other anchors, cartridges, magazines, etc. Likewise, the anchors may be used in different configurations with other working suture and suture lock arrangements, other cartridges, magazines and delivery tools. Thus the overall combination shown can be modified in a variety of ways.

Additional features and alternative designs for various components, subassemblies and assemblies may be found in the following patent applications, each of which is incorporated herein by reference:

U.S. Prov. Pat. App. No. 63/172,564, filed Apr. 8, 2021, titled KNOTLESS MICRO SUTURE ANCHORS AND ANCHOR ARRAYS FOR ANATOMICAL ATTACHMENT OF SOFT TISSUE TO BONE, and U.S. patent application Ser. No. 17/551,588, filed Dec. 15, 2021, titled KNOTLESS MICRO SUTURE ANCHORS AND ANCHOR ARRAYS FOR ANATOMICAL ATTACHMENT OF SOFT TISSUE TO BONE.

U.S. Prov. Pat. App. No. 63/172,565, filed Apr. 8, 2021, titled TENSIONABLE AND LOCKABLE MICRO SUTURE ANCHORS AND ANCHOR ARRAYS FOR ANATOMICAL ATTACHMENT OF SOFT TISSUE TO BONE, and U.S. patent application Ser. No. 17/551,709, filed Dec. 15, 2021, titled TENSIONABLE AND LOCKABLE MICRO SUTURE ANCHORS AND ANCHOR ARRAYS FOR ANATOMICAL ATTACHMENT OF SOFT TISSUE TO BONE.

U.S. Prov. Pat. App. No. 63/172,613, filed Apr. 8, 2021, titled KNOTLESS MICRO SUTURE ANCHOR ARRAY FOR HIGH DENSITY ANATOMICAL ATTACHMENT OF SOFT TISSUE TO BONE, and U.S. patent application Ser. No. 17/551,728, filed Dec. 15, 2021, titled KNOTLESS MICRO SUTURE ANCHOR ARRAY FOR HIGH DENSITY ANATOMICAL ATTACHMENT OF SOFT TISSUE TO BONE.

U.S. Prov. Pat. App. No. 63/172,614, filed Apr. 8, 2021, titled METHOD FOR CREATING A TENSIONABLE AND LOCKABLE SUTURE ANCHOR ARRAY FOR ANATOMICAL ATTACHMENT OF SOFT TISSUE TO BONE, and U.S. patent application Ser. No. 17/551,779, filed Dec. 15, 2021, titled METHOD FOR CREATING A TENSIONABLE AND LOCKABLE SUTURE ANCHOR ARRAY FOR ANATOMICAL ATTACHMENT OF SOFT TISSUE TO BONE.

U.S. Prov. Pat. App. No. 63/172,629, filed Apr. 8, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. patent application Ser. No. 17/551,811, filed Dec. 15, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE.

U.S. Prov. Pat. App. No. 63/172,624, filed Apr. 8, 2021, titled CARTRIDGE DEVICE FOR SUTURE ANCHOR AND SUTURE MANAGEMENT DURING IMPLANTATION OF A MICRO SUTURE ANCHOR ARRAY, and U.S. patent application Ser. No. 17/551,838, Filed Dec. 15, 2021, titled CARTRIDGE DEVICE FOR SUTURE ANCHOR AND SUTURE MANAGEMENT DURING IMPLANTATION OF A MICRO SUTURE ANCHOR ARRAY.

U.S. Prov. Pat. App. No. 63/172,630, filed Apr. 8, 2021, titled METHODS FOR TRANSTENDINOUS IMPLANTATION OF KNOTLESS MICRO SUTURE ANCHORS AND ANCHOR ARRAYS, and U.S. patent application Ser. No. 17/551,885, filed Dec. 15, 2021, titled METHODS FOR TRANSTENDINOUS IMPLANTATION OF KNOTLESS MICRO SUTURE ANCHORS AND ANCHOR ARRAYS.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. An assembly for locking a slidable working suture when tensioned in a suture anchor during tissue fixation to bone comprising:
   an anchor body having at least one suture receiving passage therethrough and a second passage therethrough;

a working suture passing through each suture receiving passage wherein the working suture flosses through each suture receiving passage when tension is applied to the working suture; and a locking cord extending through the second passage, the locking cord having a collapsible loop extending out the second passage and encircling a portion of the working suture, wherein the collapsible loop is configured to collapse and thereby apply force to the working suture to lock the working suture in a fixed position relative to the anchor body; and wherein the locking cord is independent of the working suture.

2. The assembly of claim 1, wherein the locking cord comprises a suture having at least a slidable knot tied therein to form the collapsible loop to allow collapsing of the loop when a tightening leg through the second passage is tensioned.

3. The assembly of claim 2, wherein the second passage has an upper portion for receiving the slidable knot at least partially therein that terminates in a platform within the second passage that does not allow passage of the slidable knot.

4. The assembly claim 3, wherein the locking loop includes first and second legs, and the second passage includes a lower portion having an oval shape for allowing both legs of the locking loop to pass therethrough side by side and out the passage.

5. The assembly of claim 4, wherein the slidable knot is at least a 4-throw uni knot.

6. The assembly of claim 4, wherein the second passage oval portion is sized to allow movement of at least a portion of the working suture to be pulled therein in response to tension on the locking cord.

7. The assembly of claim 1, wherein the working suture is a braided multistrand suture having a compressible cross-sectional area that reduces by at least about 25% when the locking loop is tightened during use.

8. The assembly of claim 7, wherein the working suture is a round No. 2 suture.

9. A plurality of assemblies for locking a tensioned suture on each of a plurality of suture anchors in a continuous single suture pre-strung chain of suture anchors for affixing tissue to bone comprising:

a plurality of anchor bodies, each anchor body having at least one suture receiving passage and a second passage therethrough;

a single working suture passing through each of the suture receiving passages of the plurality of anchor bodies, wherein the working suture flosses through each suture receiving passage when tension is applied to the working suture;

a plurality of locking cords, a single separate locking cord extending through the second passage of each of the anchor bodies, the locking cord having a collapsible locking loop extending out the second passage and encircling a portion of the working suture, wherein collapsing the locking loop fixes the working suture relative to the anchor body.

10. The plurality of assemblies of claim 9, wherein each of the locking cords comprise a suture having at least a slidable knot tied therein to form the locking loop to allow collapsing of the locking loop when a tightening leg through the second passage is tensioned.

11. The plurality of assemblies of claim 10, wherein each of the second passages have an upper portion for receiving the slidable knot at least partially therein that terminates in a platform within the second passage that does not allow passage of the slidable knot.

12. The plurality of assemblies of claim 11, wherein each locking loop includes first and second legs, and each of the second passages include a lower portion having an oval shape for allowing both legs of the locking loop to pass therethrough side by side and out the passage.

13. The plurality of assemblies of claim 10, wherein the slidable knot is at least a 4-throw uni knot.

14. The plurality of assemblies of claim 13, wherein each of the second passage oval portions are sized to allow movement of at least a portion of the working suture to be pulled therein in response to tension on the locking cord.

15. The plurality of assemblies of claim 14, wherein the working suture is a braided multistrand suture having a compressible cross-sectional area that reduces by at least about 25% when the locking loop is tightened during use.

16. The plurality of assemblies of claim 15, wherein the working suture is a round No. 2 suture.

17. A method for locking a working suture in a fixed position relative to a suture anchor through which the working suture is tensioned during tissue fixation to bone, the method comprising the steps of:

providing an anchor body having at least one suture receiving passage therethrough with a working suture passing through each suture receiving passage wherein the working suture flosses through each suture receiving passage when tension is applied to the working suture, the anchor body further including at least one second passage through the anchor body, with a locking cord extending through the second passage, the locking cord having a collapsible locking loop extending out of the second passage and encircling a portion of the working suture, wherein the locking cord is independent of the working suture;

tensioning the working suture by applying force; and, collapsing the locking loop to lock the working suture in place.

18. The method of claim 17, wherein a plurality of anchors are pre-strung on the working suture, each of the plurality of anchors having a locking loop, and the working suture is implanted by sequentially performing the tensioning and collapsing steps for the plurality of anchors to create a plurality of tensioned suture bridges between anchor bodies.

19. The method of claim 18, wherein the collapsible locking loop is formed from a suture having a slidable knot formed therein.

20. The method claim 19, wherein the slidable knot is at least a 4-throw uni knot.

* * * * *